(12) United States Patent
Huang et al.

(10) Patent No.: US 7,070,921 B2
(45) Date of Patent: Jul. 4, 2006

(54) MOLECULAR MODIFICATION ASSAYS

(75) Inventors: Wei Huang, Santa Clara, CA (US); Merl F. Hoekstra, Cardiff By The Sea, CA (US); J. Richard Sportsman, Palo Alto, CA (US); Ewald A. Terpetschnig, Austin, TX (US)

(73) Assignee: Molecular Devices Corporation, Sunnyvale, CA (US)

( * ) Notice: Subject to any disclaimer, the term of this patent is extended or adjusted under 35 U.S.C. 154(b) by 0 days.

(21) Appl. No.: 09/844,655

(22) Filed: Apr. 27, 2001

(65) Prior Publication Data

US 2002/0034766 A1 Mar. 21, 2002

Related U.S. Application Data

(63) Continuation of application No. 09/596,444, filed on Jun. 19, 2000, and a continuation of application No. PCT/US00/16025, filed on Jun. 9, 2000.

(60) Provisional application No. 60/241,032, filed on Oct. 17, 2000, provisional application No. 60/223,642, filed on Aug. 8, 2000, and provisional application No. 60/200,594, filed on Apr. 28, 2000.

(51) Int. Cl.
*G01N 21/75* (2006.01)

(52) U.S. Cl. .............................. 435/4; 435/6; 435/7.1; 435/91.1; 435/91.2; 435/283.1; 435/285.2; 435/287.2; 436/164; 436/171; 436/172; 436/800; 436/805

(58) Field of Classification Search .................. 435/4, 435/6, 7.1, 91.1, 91.2, 283.1, 285.2, 287.2; 436/164, 171, 172, 800, 805

See application file for complete search history.

(56) References Cited

U.S. PATENT DOCUMENTS

| | | |
|---|---|---|
| 3,135,793 A | 6/1964 | Bruce et al. |
| 3,214,377 A | 10/1965 | Hotten |
| 3,504,052 A | 3/1970 | Neuse et al. |
| 3,530,049 A | 9/1970 | Scherzer et al. |
| 3,901,654 A | 8/1975 | Gross |
| 3,925,162 A | 12/1975 | Kanno |
| 3,966,556 A | 6/1976 | Rubenstein et al. |
| 3,996,345 A | 12/1976 | Ullman et al. |
| 4,163,780 A | 8/1979 | Ishida et al. |
| 4,181,654 A | 1/1980 | Weitl et al. |
| 4,199,559 A | 4/1980 | Ullman et al. |
| 4,205,952 A | 6/1980 | Cais |
| 4,220,722 A | 9/1980 | Rowley et al. |
| 4,238,195 A | 12/1980 | Boguslaski et al. |
| 4,238,395 A | 12/1980 | Buckler et al. |
| 4,240,751 A | 12/1980 | Linnecke et al. |
| 4,257,774 A | 3/1981 | Richardson et al. |
| 4,277,437 A | 7/1981 | Maggio |

(Continued)

FOREIGN PATENT DOCUMENTS

| | | |
|---|---|---|
| CA | 2099542 | 1/1994 |
| EP | 0 137 457 A2 | 4/1985 |
| EP | 0 178 450 A2 | 4/1986 |
| EP | 0 204 109 | 4/1986 |
| EP | 0 259 386 B1 | 2/1987 |
| EP | 0 242 847 A2 | 10/1987 |
| EP | 0 278 149 A2 | 8/1988 |
| EP | 0 317 074 B1 | 10/1988 |
| EP | 0 312 897 A1 | 4/1989 |
| EP | 0 382 433 B1 | 8/1990 |
| EP | 0 578 067 A1 | 6/1993 |
| EP | 0639647 | 2/1995 |
| EP | 0678581 | 10/1995 |
| EP | 0 382 433 A2 | 12/1996 |
| EP | 0774515 | 5/1997 |
| EP | 0774516 | 5/1997 |
| EP | 0457213 | 7/1997 |
| EP | 0 648 280 B1 | 5/1999 |

(Continued)

OTHER PUBLICATIONS

*Adaptation of Fluorescence Polaration Immunoassay to the Assay of Macromolecules*, Urios et al., Analytical Biochemistry, vol. 185, No. 2, pp. 308–312, Mar. 1990.

*Direction Observation of the Biphasic Conformational Change of DNA Induced by Cationic Polymers*, Minagawa et al., FEBS, vol. 295, No. 1–3, pp. 67–69, Dec. 1991.

*Accessibility of Nucleic Acid–Complexed Biomolecules to Hydroxyl Radicals Correlates With Their Conformation: A Fluorescence Polarization Spectroscopy Study*, Makrigiorgos et al., International Journal of Radiation Biology, vol. 66, No. 3, pp. 247–257, Sep. 1994.

*A Fluorimetric Method for the Detection of Cooper–Mediated Hydroxyl Free Radicals in the Immediate Proximity of DNA*, Makrigiorgos et al., Free Radical Biology & Medicine, vol. 18, No. 4, pp. 669–678, Apr. 1995.

*Gmelin: Handbook of Inorganic and Organometallic Chemistry: Ga Gallium: Supplement vol. D 3 Coordination Compounds 3*, Kotowski et al., pp. 152–170, 202, 209, and 262, Nov. 1995.

*Application of Fluorescence Polarization Assays in High–Throughput Screening*, Owicki et al., Genetic Engineering News, vol. 17, No. 19, pp. 1–3, 1997.

*Chemistry of the Elements, Second Edition*, Greenwood et al., pp. 905–925, 1997.

*Homogeneous Proximity Tyrosine Kinase Assays: Scintillation Proximity Assay Versus Homogeneous Time–Resolved Fluorescence*, Park et al., Analytical Biochemistry, vol. 269, No. 1, pp. 94–104, Apr. 1999.

(Continued)

*Primary Examiner*—Long V. Le
*Assistant Examiner*—Jacob Cheu
(74) *Attorney, Agent, or Firm*—Kolisch Hartwell, P.C.

(57) ABSTRACT

Assays for detecting molecular modifications such as phosphate modifications and the presence and/or activity of enzymes and other agents involved in facilitating or otherwise regulating such modifications.

21 Claims, 10 Drawing Sheets

U.S. PATENT DOCUMENTS

| | | |
|---|---|---|
| 4,280,815 A | 7/1981 | Oberhardt et al. |
| 4,293,310 A | 10/1981 | Weber |
| 4,318,846 A | 3/1982 | Khanna et al. |
| 4,352,395 A | 10/1982 | Sydansk |
| 4,352,751 A | 10/1982 | Wieder et al. |
| 4,363,759 A | 12/1982 | Boguslaski et al. |
| 4,372,745 A | 2/1983 | Mandle et al. |
| 4,374,120 A | 2/1983 | Soini et al. |
| 4,378,344 A | 3/1983 | Zahradnik et al. |
| 4,412,064 A | 10/1983 | Hinman |
| 4,419,453 A | 12/1983 | Dorman et al. |
| 4,425,427 A | 1/1984 | Luderer |
| 4,432,907 A | 2/1984 | Wieder et al. |
| 4,459,360 A | 7/1984 | Marinkovich |
| 4,490,216 A | 12/1984 | McConnell |
| 4,492,762 A | 1/1985 | Wang et al. |
| 4,514,508 A | 4/1985 | Hirschfeld |
| 4,542,104 A | 9/1985 | Stryer et al. |
| 4,547,527 A | 10/1985 | Ingram |
| 4,565,790 A | 1/1986 | Hemmilä et al. |
| 4,587,223 A | 5/1986 | Soini et al. |
| 4,637,988 A | 1/1987 | Hinshaw et al. |
| 4,652,440 A | 3/1987 | Paik et al. |
| 4,656,127 A | 4/1987 | Mundy |
| 4,659,839 A | 4/1987 | Nicolotti et al. |
| 4,670,572 A | 6/1987 | Hinshaw et al. |
| 4,687,732 A | 8/1987 | Ward et al. |
| 4,687,747 A | 8/1987 | Lin |
| 4,699,978 A | 10/1987 | Barton |
| 4,704,353 A | 11/1987 | Humphries et al. |
| 4,707,440 A | 11/1987 | Stavrianopoulos |
| 4,711,955 A | 12/1987 | Ward et al. |
| 4,721,669 A | 1/1988 | Barton |
| 4,741,900 A | 5/1988 | Alvarez et al. |
| 4,745,076 A | 5/1988 | Müller et al. |
| 4,751,190 A | 6/1988 | Chiapetta et al. |
| 4,761,481 A | 8/1988 | Hale et al. |
| 4,772,548 A | 9/1988 | Stavrianopoulos |
| 4,801,804 A | 1/1989 | Rosenthal |
| 4,806,488 A | 2/1989 | Berger, Jr. et al. |
| 4,808,541 A | 2/1989 | Mikola et al. |
| 4,822,733 A | 4/1989 | Morrison |
| 4,830,786 A | 5/1989 | Pease et al. |
| 4,849,330 A | 7/1989 | Humphries et al. |
| 4,851,331 A | 7/1989 | Vary et al. |
| 4,859,609 A | 8/1989 | Dull et al. |
| 4,863,849 A | 9/1989 | Melamede |
| 4,863,876 A | 9/1989 | Hevey |
| 4,876,190 A | 10/1989 | Recktenwald |
| 4,876,335 A | 10/1989 | Yamane et al. |
| 4,883,579 A | 11/1989 | Humphries et al. |
| 4,894,347 A | 1/1990 | Hillyard et al. |
| 4,915,812 A | 4/1990 | Parce et al. |
| 4,920,195 A | 4/1990 | Kankare et al. |
| 4,942,127 A | 7/1990 | Wada et al. |
| 4,943,523 A | 7/1990 | Stavrianopoulos |
| 4,946,958 A | 8/1990 | Campbell et al. |
| 4,956,275 A | 9/1990 | Zuk et al. |
| 4,962,020 A | 10/1990 | Tabor et al. |
| 4,963,658 A | 10/1990 | Kung et al. |
| 4,966,917 A | 10/1990 | White |
| 4,978,608 A | 12/1990 | Kung et al. |
| 5,004,806 A | 4/1991 | Kung |
| 5,011,770 A | 4/1991 | Kung et al. |
| 5,030,576 A | 7/1991 | Dull et al. |
| 5,032,677 A | 7/1991 | Hale et al. |
| 5,055,578 A | 10/1991 | Hale et al. |
| 5,077,037 A | 12/1991 | Wallace |
| 5,086,002 A | 2/1992 | Hillyard et al. |
| 5,104,804 A | 4/1992 | Humphries et al. |
| 5,106,957 A | 4/1992 | Hale et al. |
| 5,112,134 A | 5/1992 | Chow et al. |
| 5,116,989 A | 5/1992 | Hale et al. |
| 5,120,644 A | 6/1992 | Ikenaka et al. |
| 5,124,457 A | 6/1992 | Ungemach et al. |
| 5,141,852 A | 8/1992 | Egan et al. |
| 5,155,212 A | 10/1992 | Dubler et al. |
| 5,180,828 A | 1/1993 | Ghazarossian et al. |
| 5,202,423 A | 4/1993 | Kankare et al. |
| 5,216,134 A | 6/1993 | Mukkala et al. |
| 5,221,605 A | 6/1993 | Bard et al. |
| 5,225,543 A | 7/1993 | Eppler et al. |
| 5,232,858 A | 8/1993 | Wolfbeis et al. |
| 5,235,039 A | 8/1993 | Heath et al. |
| 5,238,808 A | 8/1993 | Bard et al. |
| 5,245,038 A | 9/1993 | Hale et al. |
| 5,246,867 A | 9/1993 | Lakowicz et al. |
| 5,252,293 A | 10/1993 | Drbal et al. |
| 5,252,462 A | 10/1993 | Drevin et al. |
| 5,252,740 A | 10/1993 | Hale et al. |
| 5,256,535 A | 10/1993 | Ylikoski et al. |
| 5,258,512 A | 11/1993 | Heiman et al. |
| 5,260,200 A | 11/1993 | Kahn et al. |
| 5,260,441 A | 11/1993 | Heiman et al. |
| 5,270,171 A | 12/1993 | Cercek et al. |
| 5,274,113 A | 12/1993 | Kang et al. |
| 5,278,048 A | 1/1994 | Parce et al. |
| 5,279,943 A | 1/1994 | Mathis et al. |
| 5,283,173 A | 2/1994 | Fields et al. |
| 5,302,509 A | 4/1994 | Cheeseman |
| 5,310,687 A | 5/1994 | Bard et al. |
| 5,312,986 A | 5/1994 | Simon et al. |
| 5,315,015 A | 5/1994 | Hui et al. |
| 5,316,909 A | 5/1994 | Xu |
| 5,324,825 A | 6/1994 | Kankare et al. |
| 5,326,692 A | 7/1994 | Brinkley et al. |
| 5,340,714 A | 8/1994 | Katsilometes |
| 5,340,716 A | 8/1994 | Ullman et al. |
| 5,341,215 A | 8/1994 | Seher |
| 5,369,108 A | 11/1994 | Breslow et al. |
| 5,374,531 A | 12/1994 | Jensen |
| 5,384,108 A | 1/1995 | Rajagopalan |
| 5,393,659 A | 2/1995 | Noah et al. |
| 5,403,928 A | 4/1995 | Arrhenuis |
| 5,409,666 A | 4/1995 | Nagel et al. |
| 5,409,835 A | 4/1995 | Lakowicz et al. |
| 5,433,896 A | 7/1995 | Kang et al. |
| 5,434,088 A | 7/1995 | Ikeda et al. |
| 5,443,791 A | 8/1995 | Cathcart et al. |
| 5,445,935 A | 8/1995 | Royer |
| 5,453,356 A | 9/1995 | Bard et al. |
| 5,457,186 A | 10/1995 | Mukkala et al. |
| 5,464,607 A | 11/1995 | Anelli et al. |
| 5,466,578 A | 11/1995 | Kidwell |
| 5,478,754 A | 12/1995 | Brandt et al. |
| 5,482,699 A | 1/1996 | Almen et al. |
| 5,494,793 A | 2/1996 | Schindele et al. |
| 5,501,956 A | 3/1996 | Wada et al. |
| 5,512,493 A | 4/1996 | Mathis et al. |
| 5,518,900 A | 5/1996 | Nikiforov et al. |
| 5,525,479 A | 6/1996 | Anthony et al. |
| 5,527,684 A | 6/1996 | Mabile et al. |
| 5,527,688 A | 6/1996 | Mallia |
| 5,531,978 A | 7/1996 | Berg et al. |
| 5,538,858 A | 7/1996 | Mallia et al. |
| 5,541,113 A | 7/1996 | Siddigi et al. |
| 5,554,749 A | 9/1996 | Wallace et al. |
| 5,561,051 A | 10/1996 | Silverman |
| 5,561,052 A | 10/1996 | Koike |
| 5,567,302 A | 10/1996 | Song et al. |
| 5,571,684 A | 11/1996 | Lawrence et al. |

| | | | | | | |
|---|---|---|---|---|---|---|
| 5,571,897 A | 11/1996 | Takalo et al. | | 5,849,547 A | 12/1998 | Cleuziat et al. |
| 5,573,752 A | 11/1996 | Ranganathan et al. | | 5,849,794 A | 12/1998 | Bianchi et al. |
| 5,591,581 A | 1/1997 | Massey et al. | | 5,852,191 A | 12/1998 | Karandikar et al. |
| 5,593,867 A | 1/1997 | Walker et al. | | 5,853,999 A | 12/1998 | Olsson et al. |
| 5,599,681 A | 2/1997 | Epstein et al. | | 5,854,008 A | 12/1998 | Diamandis |
| 5,610,075 A | 3/1997 | Stahl-Rees | | 5,858,671 A | 1/1999 | Jones |
| 5,610,287 A | 3/1997 | Nikiforov et al. | | 5,858,676 A | 1/1999 | Yang et al. |
| 5,614,368 A | 3/1997 | Ghazarossian et al. | | 5,858,805 A | 1/1999 | Cheng |
| 5,616,312 A | 4/1997 | Rosik | | 5,859,215 A | 1/1999 | Rodriguez-Ubis et al. |
| 5,621,075 A | 4/1997 | Kahn et al. | | 5,861,239 A | 1/1999 | Kleyn et al. |
| 5,622,821 A | 4/1997 | Selvin et al. | | 5,861,262 A | 1/1999 | Chaudiere et al. |
| 5,624,847 A | 4/1997 | Lakowicz et al. | | 5,866,335 A | 2/1999 | Katsilometes et al. |
| 5,629,157 A | 5/1997 | Goodman et al. | | 5,871,713 A | 2/1999 | Meyer et al. |
| 5,631,127 A | 5/1997 | Sundrehagen | | 5,874,214 A | 2/1999 | Nova et al. |
| 5,631,169 A | 5/1997 | Lakowicz et al. | | 5,880,096 A | 3/1999 | Barrett et al. |
| 5,632,982 A | 5/1997 | Sussman et al. | | 5,880,296 A | 3/1999 | Imbert et al. |
| 5,637,463 A | 6/1997 | Dalton et al. | | 5,885,779 A | 3/1999 | Sadowski et al. |
| 5,637,509 A | 6/1997 | Hemmilä et al. | | 5,888,728 A | 3/1999 | Olson et al. |
| 5,639,599 A | 6/1997 | Ryder et al. | | 5,888,819 A | 3/1999 | Goelet et al. |
| 5,639,615 A | 6/1997 | Selvin et al. | | 5,891,621 A | 4/1999 | Chabin et al. |
| 5,641,633 A | 6/1997 | Linn et al. | | 5,891,674 A | 4/1999 | Hillman et al. |
| 5,641,878 A | 6/1997 | Dandliker et al. | | 5,891,696 A | 4/1999 | Shaw et al. |
| 5,645,800 A | 7/1997 | Masterson et al. | | 5,897,674 A | 4/1999 | Jung et al. |
| 5,648,269 A | 7/1997 | Lakowicz et al. | | 5,910,574 A | 6/1999 | Presta et al. |
| 5,656,254 A | 8/1997 | Ramalingam et al. | | 5,912,137 A | 6/1999 | Tsien et al. |
| 5,656,433 A | 8/1997 | Selvin et al. | | 5,914,230 A | 6/1999 | Liu et al. |
| 5,660,991 A | 8/1997 | Lakowicz et al. | | 5,945,283 A | 8/1999 | Kwok et al. |
| 5,668,110 A | 9/1997 | Barrett et al. | | 5,948,620 A | 9/1999 | Hurd et al. |
| 5,670,113 A | 9/1997 | Akong et al. | | 5,958,694 A | 9/1999 | Nikiforov |
| 5,676,943 A | 10/1997 | Baetge et al. | | 5,962,243 A | 10/1999 | Brown et al. |
| 5,677,196 A | 10/1997 | Herron et al. | | 5,981,180 A | 11/1999 | Chandler et al. |
| 5,677,199 A | 10/1997 | Arrhenuis | | 5,981,185 A | 11/1999 | Matson et al. |
| 5,677,280 A | 10/1997 | Barrett et al. | | 5,985,550 A | 11/1999 | Goodman et al. |
| 5,683,983 A | 11/1997 | Barrett et al. | | 5,989,835 A | 11/1999 | Dunlay et al. |
| 5,705,045 A | 1/1998 | Park et al. | | 6,004,744 A | 12/1999 | Goelet et al. |
| 5,707,813 A | 1/1998 | Dandliker et al. | | 6,005,113 A | 12/1999 | Wu et al. |
| 5,711,915 A | 1/1998 | Siegmund et al. | | 6,007,984 A | 12/1999 | Wang et al. |
| 5,723,304 A | 3/1998 | Abuknesha | | 6,013,431 A | 1/2000 | Söderlund et al. |
| 5,731,147 A | 3/1998 | Bard et al. | | 6,013,457 A | 1/2000 | Neunhofer et al. |
| 5,738,825 A | 4/1998 | Rudigier et al. | | 6,022,708 A | 2/2000 | de Sauvage et al. |
| 5,739,001 A | 4/1998 | Brown et al. | | 6,025,129 A | 2/2000 | Nova et al. |
| 5,741,714 A | 4/1998 | Liberti | | 6,037,136 A | 3/2000 | Beach et al. |
| 5,741,715 A | 4/1998 | Ghoshal et al. | | 6,045,755 A | 4/2000 | Lebl et al. |
| 5,744,320 A | 4/1998 | Sherf et al. | | 6,045,996 A | 4/2000 | Cronin et al. |
| 5,750,410 A | 5/1998 | Dou et al. | | 6,054,557 A | 4/2000 | Faure et al. |
| 5,756,292 A | 5/1998 | Royer | | 6,071,748 A | 6/2000 | Modlin et al. |
| 5,756,304 A | 5/1998 | Jovanovich | | 6,137,584 A | 10/2000 | Seidel et al. |
| 5,760,188 A | 6/1998 | Beaudet et al. | | 6,451,871 B1 | 9/2002 | Winterton et al. |
| 5,762,910 A | 6/1998 | Unger et al. | | 6,472,141 B1 | 10/2002 | Nikiforov |
| 5,763,158 A | 6/1998 | Bohannon | | 6,703,498 B1 | 3/2004 | Tchaga |
| 5,770,455 A | 6/1998 | Cargill et al. | | | | |
| 5,773,257 A | 6/1998 | Nielson et al. | | | FOREIGN PATENT DOCUMENTS | |
| 5,783,397 A | 7/1998 | Hughes et al. | | | | |
| 5,783,687 A | 7/1998 | Glazer et al. | | EP | 0650521 | 3/2001 |
| 5,786,139 A | 7/1998 | Burke et al. | | GB | 2 223 096 A | 8/1989 |
| 5,798,085 A | 8/1998 | Seaton et al. | | JP | 1-143874 | 6/1989 |
| 5,800,778 A | 9/1998 | Chen et al. | | JP | 1-231898 | 9/1989 |
| 5,800,989 A | 9/1998 | Linn et al. | | JP | 2-295496 | 12/1990 |
| 5,800,996 A | 9/1998 | Lee et al. | | JP | 5-123196 | 5/1993 |
| 5,801,149 A | 9/1998 | Shoelson | | JP | 6-43159 | 2/1994 |
| 5,804,395 A | 9/1998 | Schade et al. | | WO | WO81/00261 | 2/1981 |
| 5,807,522 A | 9/1998 | Brown et al. | | WO | WO81/01883 | 7/1981 |
| 5,811,256 A | 9/1998 | Bryant | | WO | WO87/07385 | 12/1987 |
| 5,820,849 A | 10/1998 | Schmitt-Willich et al. | | WO | WO88/06633 | 9/1988 |
| 5,824,517 A | 10/1998 | Cleuziat et al. | | WO | WO90/05301 | 5/1990 |
| 5,824,557 A | 10/1998 | Burke et al. | | WO | WO91/13075 | 9/1991 |
| 5,824,772 A | 10/1998 | Vincent et al. | | WO | WO92/11039 | 7/1992 |
| 5,827,653 A | 10/1998 | Sammes et al. | | WO | WO92/15712 | 9/1992 |
| 5,830,769 A | 11/1998 | Wieder et al. | | WO | WO93/10461 | 5/1993 |
| 5,846,710 A | 12/1998 | Bajaj | | WO | WO93/19206 | 9/1993 |
| 5,846,722 A | 12/1998 | Kauvar et al. | | WO | WO93/25672 | 12/1993 |
| | | | | WO | WO95/12607 | 5/1995 |

| | | |
|---|---|---|
| WO | WO95/21271 | 8/1995 |
| WO | WO96/03410 | 2/1996 |
| WO | WO97/22719 | 6/1997 |
| WO | WO97/35033 | 9/1997 |
| WO | WO97/40104 | 10/1997 |
| WO | WO97/45539 | 12/1997 |
| WO | WO97/45739 | 12/1997 |
| WO | WO98/01472 | 1/1998 |
| WO | WO98/05962 | 2/1998 |
| WO | WO98/12156 | 3/1998 |
| WO | WO98/18956 | 5/1998 |
| WO | WO98/23942 | 6/1998 |
| WO | WO98/45481 | 10/1998 |
| WO | WO98/59066 | 12/1998 |
| WO | WO99/11774 | 3/1999 |
| WO | WO99/23466 | 5/1999 |
| WO | WO99/29894 | 6/1999 |
| WO | WO99/31431 | 6/1999 |
| WO | WO99/36779 | 7/1999 |
| WO | WO99/60383 | 11/1999 |
| WO | WO99/60385 | 11/1999 |
| WO | WO00/00819 | 1/2000 |
| WO | WO00/06989 | 2/2000 |
| WO | WO00/06990 | 2/2000 |
| WO | WO00/06991 | 2/2000 |
| WO | WO00/11220 | 3/2000 |
| WO | WO00/14515 | 3/2000 |
| WO | WO00/23785 | 4/2000 |
| WO | WO00/42209 | 7/2000 |
| WO | WO00/47693 | 8/2000 |
| WO | WO00/48990 | 8/2000 |
| WO | WO00/48991 | 8/2000 |
| WO | WO00/55372 | 9/2000 |
| WO | WO00/66269 | 11/2000 |
| WO | WO00/75167 | 12/2000 |
| WO | WO00/75662 | 12/2000 |
| WO | WO00/75664 | 12/2000 |

OTHER PUBLICATIONS

*Fluorescence Polarization and Anisotropy in High Throughput Screening: Perspectives and Primer,* Owicki, *Journal of Biomolecular Screening,* vol. 5, No. 5, pp. 297–306, Oct. 2000.

*Microchip–Based Systems for Target Validation and HTS,* Sundberg et al., *Drug Discovery Today,* vol. 5, No. 12, (Suppl.), pp. S92–103, Dec. 2000.

*What is Coordination Compound?,* internet printouts, pp. 1–5, Jun. 9, 2002 (print date).

*Mobility Shift Screening Assays for Protein Kinase Targets,* Kotturi et al., *American Laboratory,* pp. 32, 34, 36, and 38–39, Feb. 2003.

*A Homogeneous Fluorescence Polarization Assay Adaptable for a Range of Protein Serine/Threonine and Tyrosine Kinases,* Gaudet et al., *Journal of Biomolecular Screening,* vol. 8, No. 2, pp. 164–175, Apr. 2003.

*Analyst® GT Multimode Reader,* Molecular Devices Corporation, brochure, pp. 1–2, 2003.

*Homogeneous Cell–Based Fluorescence Polarization Assay for the Direct Ditection of cAMP,* Prystay et al., *Journal of Biomolecular Screening,* vol. 6, No. 2, pp. 75–82, 2001.

*A Homogeneous High Throughput Nonradioactive Method for Measurement of Functional Activity of $G_2$ –Coupled Receptors in Membranes,* Allen et al., *Journal of Biomolecular Screening,* vol. 7, No. 1, pp. 35–44, 2002.

*A Fluorescence Polarization Assay for Cyclic Nucleotide Phosphodiesterases,* Huang et al., *Journal of Biomolecular Screening,* vol. 7, No. 3, pp. 215–222, 2002.

Witt et al. Rapid Protein Kinase Assay Using Phosphocellulose–Paper Absorption. *Analytical Biochemistry.* 66:253–258 (1975).

Glass et al. Isolation of Phosphorylated Peptides and Proteins on Ion Exchange Papers. *Analytical Biochemistry,* 87:566–575 (1978).

Grossman. Interaction of Creatine Kinase from Monkey Brain with Substrate: Analysis of Kinetics and Fluorescence Polarization. *Journal of Neurochemistry,* 41:3. 729–736 (1983).

Porath et al. Immobilized Metal Ion Affinity Adsorption and Immobilized Metal Ion Affinity Chromatography of Biomaterials. Serum Protein Affinities for Gel–Immobilized Iron and Nickel Ions. *Biochemistry.* 22:1621–1630 (1983).

Muszyńska et al. Selective Adsorption of Phosphoproteins on Gel–Immobilized Ferric Chelate. *Biochemistry.* 25:22. 6850–6853 (1986).

Pagani et al. Fluorescence Polarization Immunoassay to Determine Aminoglycoside Modifying Enzymes Activity. *Microbiologica.* 9:423–430 (1986).

Valtorta et al. A Solid–Phase Assay for the Phosphorylation of Proteins Blotted on Nitrocellulose Membrane Filters. *Analytical Biochemistry.* 158:130–137 (1986).

Mekras et al. The Interaction of Papain with Polycations. *J. Pharm. Pharmacol.,* 41:22–26 (1989).

Blode et al. A Quantitative Assay for Tyrosine Sulfation and Tyrosine Phosphorylation in Peptides. *Biol. Chem.* 371:145–151 (Feb. 1990).

Cook et al. Detection of Protein–DNA Complex Formation by Time–Resolved Fluorescence Depolarization of Bound Ethidium Bromide. *Analytical Biochemistry.* 190:331–339 (1990).

Babcook et al. Automated Nonisotopic Assay for Protein–Tyrosine Kinase and Protein–Tyrosine Phosphatase Activities. *Analytical Biochemistry.* 196:245–251 (1991).

Muszyńka et al. Model Studies on Iron(III) Ion Affinity Chromatography. *Journal of Chromatography.* 604:19–28 (1992).

Volonté et al. Rapid Measurement of Protein Kinase and Phosphatase Activities by Slot–Filtration. *BioTechniques.* 12:6. 854–863 (1992).

Erickson et al. Metal ($Fe^{3+}$) Affinity Chromotography: Differential Adsorption of Tau Phosphoproteins. *Journal of Neuroscience Methods.* 46:245–249 (1993).

Toomik et al. Protein Kinase Assay Using Tritiated Peptide Substrates and Ferric Adsorbent Paper for Phosphopeptide Binding. *Analytical Biochemistry.* 209:348–353 (1993).

Cavatorta et al. Myelin Basic Protein Interaction with Zinc and Phosphate: Fluorescence Studies on the Water–Soluble Form of the Protein. *Biophysical Journal.* 66:1174–1179 (Apr. 1994).

Checovich et al. Fluorescence Polarization—A New Tool for Cell and Molecular Biology. *Nature.* 375:254–256 (May 18, 1995).

Mathis. Probing Molecular Interactions with Homogeneous Techniques Based on Rare Earth Cryptates and Fluorescence Energy Transfer. *Clinical Chemistry.* 41:9. 1391–1397 (Sep. 1995).

Boutin. Tyrosine Protein Kinase Assays. *Journal of Chromatography B.* 684:179–199 (1996).

Heyduk et al. Fluorescence Anisotropy: Rapid, Quantitative Assay for Protein–DNA and Protein–Protein Interaction. *Methods in Enzymology.* 274:492–503 (1996).

Lundblad et al. Fluorescence Polarization Analysis of Protein–DNA and Protein–Protein Interactions. *Molecular Endocrinology.* 10:6. 607–612 (1996).

Lehel et al. A Chemiluminescent Microtiter Plate Assay for Sensitive Detection of Protein Kinase Activity. *Analytical Biochemistry.* 244:340–346 (1997).

Vereb et al. Temporally and Spectrally Resolved Imaging Microscopy of Lanthanide Chelates. *Biophysical Journal.* 74:2210–2222 (May 1998).

Posewitz et al. Immobilized Gallium(III) Affinity Chromatography of Phosphopeptides. *Analytical Biochemistry.* 71:14. 2883–2892 (Jul. 15, 1999).

Fowler et al. An Evaluation of Fluorescence Polarization and Lifetime Discriminated Polarization for High Throughput Screening of Serine/Threonine Kinases. *Analytical Biochemistry.* 308:223–231 (2002).

Gatti. Profiling Substrate Phosphorylation at the Phosphopeptide Level. *Analytical Biochemistry.* 312:40–47 (2003).

*Intramolecular Mobility of Pepsin*, Glotov et al., *Molecular Biology (Moscow),* vol. 10, No. 1, pp. 161–174, Jan.–Feb. 1976.

*Histone H1–DNA Interaction. Influence of Phosphorylation on the Interaction of Histone H1 with Linear Fragmented DNA,* Glotov et al., *Nucleic Acids Research,* vol. 4, No. 4, pp. 1065–1082, Apr. 1977.

*Histone H1—DNA Interaction. On the Mechanism of DNA Strands Crosslinking by Histone H1,* Glotov et al., *Nucleic Acids Research,* vol. 5, No. 7, pp. 2587–2605, Jul. 1978 (abstract only included).

*Molecular Biology of the Cell,* Alberts et al., pp. 58–61, 1983.

*Fluorescent–Labeled Oligonucleotide Probes: Detection of Hybrid Formation in Solution by Fluorescence Polarization Spectroscopy,* Murakami et al., *Nucleic Acids Research,* vol. 19, No. 15, pp. 4097–4102, Aug. 11, 1991.

*Design and Use of Peptide Substrates for Protein Kinases,* Kemp et al., *Methods in Enzymology,* vol. 200, pp. 121–134, 1991.

*Chromatin Condensation: Does Histone H1 Dephosphorylation Play a Role?,* Roth et al., *TIBS,* vol. 17, pp. 93–98, Mar. 1992.

*Protein Phosphatase Assay Using a Modification of the P81 Paper Protein Kinase Assay Procedure,* Abukhalaf et al., *J. Biochem. Biophys.,* vol. 26, pp. 95–104, May 1993 (abstract only included).

*PNA Hybridizes to Complementary Oligonucleotides Obeying the Watson–Crick Hydrogen–Bonding Rules,* Egholm et al., *Nature,* vol. 365, No. 6446, pp. 566–568, Oct. 7, 1993.

*DNA Detection by Strand Displacement Amplification and Fluorescence Polarization with Signal Enhancement Using a DNA Binding Protein,* Walker et al., vol. 24, No. 2, pp. 348–353, Jan. 15, 1996.

*Molecular Beacons: Probes that Fluoresce Upon Hybridization,* Tyagi et al., *Nature Biotechnology,* vol. 14, pp. 303–308, Mar. 1996.

*Effects of Cell Cycle Dependent Histone H1 Phosphorylation on Chromatin Structure and Chromatin Replication,* Halmer et al., *Nucleic Acids Research,* vol. 24, No. 8, pp. 1420–1427, Apr. 15, 1996.

*A Homogeneous Fluorescence Polarization Assay for Detection of Antibody to Brucella abortus,* Nielsen et al., *J. Immunol. Methods,* vol. 195, pp. 161–168, Sep. 9, 1996.

*BODIPY–alpha–casein, a pH–Independent Protein Substrate for Protease Assays Using Fluorescence Polarization,* Schade et al., *Anal. Biochem.,* vol. 243, No. 1, pp. 1–7, Dec. 1996.

*Thermodynamic Analysis of Monoclonal Antibody Binding to Duplex DNA,* Tanha et al., *Nucleic Acids Research,* vol. 25, No. 7, pp. 1442–1449, Apr. 1, 1997.

*A Fluorescence Polarization Based Src–SH2 Binding Assay,* Lynch et al., *Anal. Biochem.,* vol. 247, No. 1, pp. 77–82, Apr. 5, 1997.

*Measurement of Specific Protease Activity Utilizing Fluorescence Polarization,* Levine et al., *Anal. Biochem.,* vol. 247, No. 1, pp. 83–88, Apr. 5, 1997.

*Dynamic Fluorescence Spectroscopy on Single Tryptophan Mutants of EII (mtl) in Detergent Micelles. Effects of Substrate Binding and Phosphorylation on the Fluorescence and Anisotropy Decay,* Dijkstra et al., *Biochemistry,* vol. 36, No. 16, pp. 4860–4866, Apr. 22, 1997.

*A Homogeneous, Fluorescence Polarization Assay for Src–Family Tyrosine Kinases,* Seethala et al., *Anal. Biochem.,* vol. 253, No. 2, pp. 210–218, Nov. 15, 1997.

*Fluorescence Polarization Colloid Charge Titration: Development and Application for Feed Forward Coagulant Control at Water Treatment Facilities* (Thesis), Green, *University of Colorado Graduate School,* approved Dec. 11, 1997.

*Fluorescence Polarization Applications Guide: DNA–Protein Binding Applications,* Panvera Corporation, pp. 2–1 to 2–9, Jan. 1998.

*A Fluorescence Polarization Competition Immunoassay for Tyrosine Kinases,* Seethala et al., *Analytical Biochemistry,* vol. 255, No. 2, pp. 257–262, Jan. 15, 1998.

*Multicolor Molecular Beacons for Allele Discrimination,* Tyagi et al., *Nature Biotechnology,* vol. 16, pp. 49–53, Jan. 16, 1998.

*Phosphorylation of the C–Terminal Sites of Human p53 Reduces Non–Sequence–Specific DNA Binding as Modeled with Synthetic Peptides,* Hoffman et al., *Biochemistry,* vol. 37, pp. 13755–13764, Sep. 29, 1998.

*Tyr'd and True: Immunochemical Reagents and Kits for Studying Tyrosine Phosphorylation,* Wilkinson, *The Scientist,* vol 13, internet printed pp. 1–9, May 10, 1999.

*U.S. Appl. No. 09/321,309 File History,* Sundberg et al., Filed May 27, 1999.

*Histone H1 GenBank Search,* Lamar, Davidson College Department of Biology, internet pp. 1–2, 2000.

*Linker Histone Binding and Displacement: Versatile Mechanism for Transcription Regulation,* Zlatanova et al., *The FASAB Journal,* vol. 14, No. 12, pp. 1697–1704, Sep. 2000.

*Escaping the Heat: A Host of Kinase Assay Formats Gives Nonradioactive Options to Researchers,* Fitzgerald, *The Scientiest,* vol. 14, internet printed pp. 1–7, Nov. 13, 2000.

*Geldanamycin Abrogates ErbB2 Association with Proteasome–Resistant β–Catenin–E–Cadherin Association, and Decreases β–Catenin–Sensitive Transcription,* Bonvini et al., *Cancer Research,* vol. 61, pp. 1671–1677, Feb. 15, 2001.

*Application Notes: Miniaturization of LANCE Kinase Assays,* PerkinElmer Live Sciences, pp. 1–3, May 2001.

*Analysis of Potential Compound Interference of AlphaScreen Signal,* Packard BioScience Inc., Application Note, pp. 1–4, Aug. 2001.

*Use of Fluorescence Polarization to Monitor MHC–Peptide Interactions in Solution,* Dedier et al., *J. Immunol. Methods,* vol. 255, pp. 57–66, Sep. 1,, 2001.

*MAP Kinase Assay,* Pedro et al. for Packard Bioscience, Inc., Application Note, pp. 1–4, Nov. 2001.

*P–Tyr–100 Insulin Receptor Tyrosine Kinase Assay,* Pedro et al. for Packard Bioscience Inc., Application Note, pp. 1–4, Nov. 2001.

*IQ Kinase Assay Products,* Pierce Biotechnology, Inc., internet printed pp. 1–8, 2002.

*Homogeneous Time–Resolved Fluorescence Product List,* CIS Bio International, 2002.

*Structural Concepts in Immunology and Immunochemistry,* Kabat, $2^{nd}$ Ed., pp. 103–105, 1976.

Joseph R. Lakowicz, Principles of Fluorescence Spectroscopy, First Edition, Sep. 1983.

*Photoelectroanalytical Chemistry: Possible Interferences in Serum and the Selective Detection of Tris(2,2'–bipyridine)ruthenium(II) in the Presence of Interferents,* Weber et al., *Clin. Chem.,* vol. 29, No. 9, pp. 1665–1672 (1983).

*Application of the Energy Gap Law to Nonradiative, Excited–State Decay,* Casper et al., *J. Phys. Chem.,* vol. 87, pp. 952–957, 1983.

*Electrogenerated Chemiluminescent Determination of $Ru(bpy)_3^{2+}$ at Low Levels,* Ege et al., *Anal. Chem.,* vol. 56, pp. 2413–2417, 1984.

*Luminescence and Redox Reactions of the Metal–to–Ligand Charge–Transfer Excited State of Tricarbonylchloro–(polypyridyl)rhenium(I) Complexes,* Kalyanasundaram, *J. Chem. Soc., Faraday Trans.,* vol. 82, pp. 2401–2415, 1986.

*Time–Resolved Fluorescence of Lanthanide Probes and Applications in Biotechnology,* Soini et al., *CRC Critical Reviews in Analytical Chemistry,* vol. 18, No. 2, 1987.

*A System for Rapid DNA Sequencing with Fluorescent Chain–Terminating Dideoxynucleotides,* Prober et al., *Science,* pp. 336–341, Oct. 16, 1987.

*Solid Phase DNA Sequencing Using the Biotin–Avidin System,* Stahl et al., *Nucleic Acids Res.,* vol. 16, No. 7, pp. 3025–3038, Apr. 11, 1988 (abstract only).

Stratagene 1988 Catalog excerpt, 1988.

*Synthetic Peptide Analogues Differentially After the Binding Affinities of Cyclic Nucleotide Dependent Protein Kinases for Nucleotide Substrates,* Bhatnagar et al., *Biochemistry,* vol. 27, No. 6, pp. 1988–1994, 1988.

*Direct Solid Phase Sequencing of Genomic and Plasmid DNA Using Magnetic Beads as Solid Support,* Hultman et al., *Nucleic Acids Res.,* vol. 17, No. 13, pp. 4937–4946, Jul. 11, 1989 (abstract only).

*RNA Sequencing Using Fluorescent–Labeled Dideoxynucleotides and Automated Fluorescence Detection,* Bauer, *Nucleic Acids Res.,* vol. 18, No. 4, pp. 879–884, Feb. 25, 1990 (abstract only).

*A Primer–Guided Nucleotide Incorporation Assay in the Genotyping of Apolipoprotein E,* Syvanen et al., *Genomics,* vol. 8, No. 4, pp. 684–692, Dec. 1990 (abstract only).

*The Unusual Origin of the Polymerase Chain Reaction,* Kary B. Mullis, *Scientific American,* pp. 56–65, Apr. 1990.

*A Brief Survey of Methods for Preparing Protein Conjugates with Dyes, Haptens, and Cross–Linking Reagents,* Brinkley, *Bioconjugate Chemistry,* vol. 3, No. 1, pp. 59–70, Jan./Feb. 1992.

*Trapped–Oligonucleotide Nucleotide Incorporation (TONI) Assay, A Simple Method for Screening Point Mutations,* Prezant et al., *Hum. Mutat.,* vol. 1, No. 2, pp. 159–164, 1992 (abstract only).

*Time–Resolved Fluorescence of a new Europium Chelate Complex: Demonstration of Highly Sensitive Detection of Protein and DNA Samples,* Saha et al., *J. Am. Chem. Soc.,* vol. 115, No. 23, pp. 11032–11033, 1993.

*Luminescent Lanthanide Complexes as Photochemical Supramolecular Devices,* Sabbatini et al., *Coordination Chemistry Reviews,* vol. 123, pp. 201–228, 1993.

*Post–Translational Modification of Proteins,* R. Krishna, *Advances in Enzymology,* 67:265–299, 1993.

*Time–Resolved Detection of Lanthanide Luminescence for Ultrasensitive Bioanalytical Assays,* Dickson et al., *J. of Photochem. Photobiol. B: Biol.,* 27 (1995) 3–19, Oct. 28, 1994.

*Processing of cDNA and Genomic Kilobase–Size Clones for Massive Screening, Mapping and Sequencing by Hybridization,* Drmanac et al., *BioTechniques,* vol. 17, No. 2, pp. 328–336, 1994.

*Synthesis of Squaraine–N–Hydroxysuccinimide Esters and Their Biological Application as Long–Wavelength Fluorescent Labels,* Terpetschnig et al., *Anal. Chem.,* vol. 217, pp. 197–204, 1994.

*Sorting Single Molecules: Application to Diagnostics and Evolutionary Biotechnology,* Eigen et al., *PNAS,* vol. 91, pp. 5740–5747, 1994.

*Fluorescence–Based DNA Minisequence Analysis for Detection of Known Single–Base Changes in Genomic DNA,* Kobayashi et al., *Mol. Cell Probes,* vol. 9, No. 3, pp. 175–182, Jun. 1995 (abstract only).

*Hybridization of Fluorescein–Labeled DNA Oligomers Detected by Fluorescence Anistropy with Protein Binding Enhancement,* Kumke et al., *Anal. Chem.,* vol. 67, No. 21, Nov. 1, 1995.

*Fluorescence Anisotropy Applied to Biomolecular Interactions,* D.M. Jameson et al., *Methods in Enzymology,* 246:283–300, 1995.

*Fluorescence Energy Transfer Immunoassay Based on a Long–Lifeline Luminescent Metal–Ligand Complex,* Young et al., *Analytical Biochemistry,* vol. 232, pp. 24–30, 1995.

*A Lifetime–Based Optical $CO_2$ Gas Sensor with Blue or Red Excitation and Stokes or Anti–Stokes Detection,* Jeffrey Sipior et al., *Analytical Biochemistry,* 227, 309–318 (1995).

*Gene Genie,* Jonathan Burke, *The Red Herring,* internet pp. 1–7, Dec. 1996.

Chemical Abstracts No. 124:160,011; abstract for Lindstroem et al., Electron transport properties in dye–sensitized nanocrystalline/nanostructured titanium dioxide films: J. Phys. Chem. vol. 100(8), pp. 3084–3088, 1996.

*Multiplex, Fluorescent, Solid–Phase Minisequencing for Efficient Screening of DNA Sequence Variation,* Pastinen et al., *Clinical Chemistry,* vol. 42, No. 9, pp. 1391–1397, 1996.

*Comparative Study of Fluorescent Ternary Terbium Complexes. Application in Enzyme Amplified Fluorimetric Immunoassay for α–fetoprotein,* Veiopoulou et al., *Analytics Chimica Acta,* vol. 335, pp. 177–184, 1996.

Chemical Abstracts No. 126:72,240; abstract for Hermann et al, "Structure of Nanocystalline TiO2 Powders and Precursor to Their Highly Efficient Photosensitizer", Chem. Mater. vol. 9 (2), pp. 430–439, 1997.

*Gene Chip Breakthrough,* David Stipp, *Fortune,* internet pp. 1–12, Mar. 31, 1997.

The Society for Biomolecular Screening, $3^{rd}$ Annual Conference and Exhibition, p. 59, Sep. 9, 22–25, 1997.

Electrochemiluminescence: A Technology Review internet pages, IGEN, printed Dec. 16, 1997.

*A Homogeneous Method for Genotyping with Fluorescence Polarization,* Gibson et al., *Clinical Chemistry,* vol. 43, No. 8, pp. 1336–1341, 1997.

*Development of Luminescent Lanthanide Chelate Labels for Diagnostic Assays,* Hemmila et al., *Journal of Alloys and Compounds,* Vo. 249, pp. 158–162, 1997.

*Minisequencing: A Specific Tool for DNA Analysis and Diagnostics on Oligonucleotide Arrays,* Pastinen et al., *Genome Research,* vol. 7, pp. 606–614, 1997.

*Template–Directed Dye–Terminator Incorporation (TDI) Assay: A Homogeneous DNA Diagnostic Method Based on Fluorescent Resonance Energy Transfer,* Chen et al., *Nucleic Acids Research,* vol. 25, No. 2, pp. 347–353, 1997.

*Towards Materials with Planned Properties: Dinuclear f–f Helicates and d–f Non Covalent Podates Based on Benzimidazole–Pyridine Binding Units,* Bunzli et al., *Journal of Alloys and Compounds,* vol. 249, pp. 14–24, 1997.

*Water Soluble Neutral calyx[4]arene–Lanthanide Complexes: Synthesis and Luminescence Properties,* Steemers et al., *J. Org. Chem.,* vol. 62, pp. 4229–4235, 1997.

*Fluorescence Polarization of Applications Guide,* Pan Vera Corporation, pp. 6–1 through 6–4, Jan. 1998 Edition.

GeneChip Probe Array Synthesis, Affymetrix, internet pp. 1–2, Mar. 17, 1998.

*Mutation Detection and Single–Molecule Counting Using Isothermal Rolling–Circle Amplification,* Lizardi et al., *Nature Genetics,* vol. 19, No. 3, pp. 225–232, Jul. 1998.

*Homogeneous Time–Resolved IL–2–IL–2Rα Assay Using Fluorescence Resonance Energy Transfer,* Stenroos et al., *Cytokine,* vol. 10, No. 7, pp. 495–499, Jul. 1998.

*Synthesis, Spectral Properties and Detection Limits of Reactive Squarylium Dyes, a New Class of Diode Laser Compatible Fluorescent Protein Labels,* Oswald et al., Aug. 21, 1998.

*Iluminating the SNP Genomic Code,* Czarnik, *Modern Drug Discovery,* pp. 49–55, Nov./Dec. 1998.

A Catalog of Reagents, Microplates and Accessories of Life Science Research, Book 2, Packard BioScience Company, Dec. 1998.

CytoFluor Fluorescence Multi–Well Plate Reader brochure, PerSeptive Biosystems, 1998.

Luc–Screen™ brochure, Tropix, Inc., 1998.

Xpress–Screen™ brochure, Tropix, Inc., 1998.

*Fixed Polarizer Ellipsometry for Simple and Sensitive Detection of Thin Films Generated by Specific Molecular Interactions: Applications in Immunoassays and DNA Sequence Detection,* Ostroff et al., *Clinical Chemistry,* 44:9, pp. 2031–2035, 1998.

*A Microfabricated Device for Sizing and Sorting DNA Molecules,* Chou et al., *PNAS,* vol. 96, pp. 11–13, Jan. 1999.

*Fluorescence Polarization in Homogeneous Nucleic Acid Analysis,* Chen et al., *Genome Research,* vol. 9, pp. 492–498, Feb. 26, 1999.

*The Human Genome Project: Challenges and Opportunities,* Washington University in St. Louis, Mar. 5, 1999.

*Everything's Great When It Sits on a Chip,* Bob Sinclair, *The Scientist,* vol. 13, #11, May 24, 1999.

*Assay Miniaturization for High–Throughput Screening,* Peter Panfili, Application Note, Sep. 1999.

CyBi™–Disk brochure, CyBio AG, Oct. 1999.

PanVera Postings, Issue 5, PanVera Corporation, Oct. 1999.

SnaPshot ddNTP Primer Extension Kit product bulletin, PE Biosystems, Oct. 1999.

Handout Information, Tips and Tricks . . . Automated Liquid–Handling in the Microplate Format, CyBio AG, Nov. 1999.

Magellan, Instrument Control and Data Analysis Software brochure, Tecan AG, Nov. 1999.

*Terbium and Rhodamine as Labels in a Homogeneous Time–Resolved Fluorometric Energy Transfer Assay of the β Subunit of Human Chorionic Gonadotropin in Serum,* Blomberg et al., *Clinical Chemistry,* vol. 45, No. 6, pp. 855–861, 1999.

TWISTER™, Tecan's Automated Microplate Handler brochure, Tecan AG, Nov. 1999.

*A Microfabricated Fluorescence–Activated Cell Sorter,* Fu et al., *Nature Biotechnology,* vol. 17, pp. 1109–1111, Nov. 1999.

Absorbance Readers brochure, Tecan AG, Dec. 1999.

*Kinase Assay Based on Thiophosphorylation and Biotinylation,* Jeong et al., *BioTechniques,* vol. 27, pp. 1232–1238, Dec. 1999.

ULTRA—The Solution for HTS and Assay Development brochure, Tecan Austria GmbH, Dec. 1999.

*Synthesis, Time–Resolved Luminescence, NMR Spectroscopy, Circular Dichroism and Circularly Polarised Luminescence Studies of Enantiopure Macrocyclic Lanthanide Tetraamide Complexes,* Dickins et al., *Chem. Eur. J.,* vol. 5, No. 3, 1999.

*Mono(di)nuclear Europium(III) Complexes of Macrobi (tri) cyclic Cryptands Derived from Diazatetralactams as Luminophores in Aqueous Solution,* Galaup et al., *Helvetica Chimica Acta,* vol. 82, pp. 543–560, 1999.

*Principles of Fluorescence Spectroscopy,* Joseph R. Kalowicz, Second Edition, 1999.

*New Fluorescence Labels for Polarization Assays and Lifetime Imaging,* Analytix, Feb. 2000.

CyBi™–PlateSafe brochure, CyBio AG, May 2000.

Protein Tyrosine Kinase Assay Kits flyer, PanVera Corporation, Jul. 2000.

Protein Kinase C Assay Kits flyer, PanVera Corporation, Jul. 2000.

Packard BioScience Company Introduces the Fusion™ Universal Microplate Analyzer press release, Packard BioScience Company, Jun. 29, 2000.

*Tris(2,2'bipyridyl)ruthenium(II)* internet pages, OMLC, printed Jul. 3, 2000.

CoreHTS, Estrogen Receptor –α & –β Competitor Assays brochure, PanVera Corporation, Jul. 2000.

Glucocorticoid Receptor flyer, PanVera Corporation, Jul. 2000.

Core HTS Glucocorticoid Receptor Competitor Assay Kit flyer, PanVera Corporation, Aug. 2000.

Fusion™, Universal Microplate Analyzer, Packard Bioscience Company, Aug. 2000.

*Development of High Throughput Screening Assays Using Fluorescence Polarization: Nuclear Receptor–Ligand–Binding and Kinase/Phosphatase Assays,* Parker et al., *Journal of Biomolecular Screening,* vol. 5, No. 2, 2000.

*Lifetime– and Color–Tailored Fluorophores in the Micro– to Millisecond Time Regime,* Chen et al., *J. Am. Chem. Soc.,* vol. 122, pp. 657–660, 2000.

*Luminescence and Structure of Europium Compounds,* Vicentini et al., *Coordination Chemistry Reviews,* vol. 196, pp. 353–382, 2000.

Reacti–Bind™ Metal Chelate Plates flyer, Pierce Chemical Company, 2000.

Reacti–Bind™ Metal Chelate High Binding Capacity Plates flyer, Pierce Chemical Company, 2000.

Reacti–Bind ™ NeutrAvidin™ High Binding Capacity (HBC) Coated Plates flyer, Pierce Chemical Company, 2000.

Reacti–Bind™ Streptavidin High Binding Capacity (HBC) Coated Plates flyer, Pierce Chemical Company, 2000.

Reacti–Bind™ NeutrAvidin™ and Streptavidin Coated Plates flyer, Pierce Chemical Company, 2000.

*Spectroscopic Properties and Design of Highly Luminescent Lanthanide Coordination Complexes,* de Sa et al., *Coordination Chemistry Reviews,* vol. 196, pp. 165–195, 2000.

Acumen Explorer brochure, Acumen, undated.

Protein Kinase C (PKC) tech specs, PanVera Corporation, undated.

PW 384 brochure, PanVera Corporation, undated.

Reacti–Bind™ Streptavidin High Binding Capacity (HBC) Coated Plates flyer, Pierce Chemical Company, 2000.

Reacti–Bind™ NeutrAvidin™ and Streptavidin Coated Plates flyer, Pierce Chemical Company, 2000.

*Spectroscopic Properties and Design of Highly Luminescent Lanthanide Coordination Complexes,* de Sa et al., *Coordination Chemistry Reviews,* vol. 196, pp. 165–195, 2000.

Acumen Explorer brochure, Acumen, undated.

Protein Kinase C (PKC) tech specs, PanVera Corporation, undated.

PW 384 brochure, PanVera Corporation, undated.

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: ARTIFICIAL SEQUENCE IS SYNTHESIZED
<220> FEATURE:
<221> NAME/KEY: MOD_RES
<222> LOCATION: (1)..(1)
<223> OTHER INFORMATION: FLUORESCEIN CONJUGATION

<400> SEQUENCE: 1

Leu Arg Arg Ala Ser Leu Gly
1               5

MOLECULAR MODIFICATION ASSAYS

CROSS-REFERENCE

This application is based upon and claims benefit under 35 U.S.C. §119(e) of the following U.S. provisional patent applications, which are incorporated herein by reference: Ser. Nos. 60/200,594, filed Apr. 28, 2000; Ser. No. 60/223,642, filed Aug. 8, 2000; and Ser. No. 60/241,032, filed Oct. 17, 2000.

This application is a continuation of and claims benefit under 35 U.S.C. §120 of the following patent applications, which are incorporated herein by reference: PCT Patent Application Ser. No. PCT/US00/16025, filed Jun. 9, 2000; and is a continuation of U.S. patent application Ser. No. 09/596,444, filed Jun. 19, 2000.

This application incorporates by reference the following U.S. patents: U.S. Pat. No. 5,843,378, issued Dec. 1, 1998; U.S. Pat. No. 6,965,381, issued Oct. 12, 1999; U.S. Pat. No. 6,071,748, issued Jun. 6, 2000; and U.S. Pat. No. 6,097,025, issued Aug. 1, 2000.

This application also incorporates by reference the following U.S. patent applications: Ser. No. 08/840,553, filed Apr. 14, 1997; Ser. No. 09/118,141, filed Jul. 16, 1998; Ser. No. 09/144,578, filed Aug. 31, 1998; Ser. No. 09/156,318, filed Sep. 18, 1998; Ser. No. 09/349,733, filed Jul. 8, 1999; Ser. No. 09/478,819, filed Jan. 5, 2000; Ser. No. 09/596,444, filed Jun. 19, 2000; Ser. No. 09/626,208, filed Jul. 26, 2000; Ser. No. 09/643,221, filed Aug. 18, 2000; Ser. No. 09/710,061, filed Nov. 10, 2000; Ser. No. 09/722,247, filed Nov. 24, 2000; Ser. No. 09/733,370, filed Dec. 8, 2000; Ser. No. 09/759,711, filed Jan. 12, 2001; Ser. No. 09/765,869, filed Jan. 19, 2001; Ser. No. 09/765,874, filed Jan. 19, 2001; Ser. No. 09/766,131, filed Jan. 19, 2001; Ser. No. 09/767,316, filed Jan. 22, 2001; Ser. No. 09/767,434, filed Jan. 22, 2001; Ser. No. 09/767,579, filed Jan. 22, 2001; Ser. No. 09/767,583, filed Jan. 22, 2001; Ser. No. 09/768,661, filed Jan. 23, 2001; Ser. No. 09/768,742, filed Jan. 23, 2001; Ser. No. 09/768,765, filed Jan. 23, 2001; Ser. No. 09/770,720, filed Jan. 25, 2001; Ser. No. 09/770,724, filed Jan. 25, 2001; Ser. No. 09/777,343, filed Feb. 5, 2001; Ser. No. 09/813,107, filed Mar. 19, 2001; Ser. No. 09/815,932, filed Mar. 23, 2001; and Ser. No. 09/836,575, filed Apr. 16, 2001 entitled Arc Lamp Power Supply, and naming David P. Stumbo as inventor.

This application also incorporates by reference the following U.S. provisional patent applications: Ser. No. 60/178,026, filed Jan. 26, 2000; Ser. Nos. 60/222,222, filed Aug. 1, 2000; Ser. No. 60/244,012, filed Oct. 27, 2000; Ser. No. 60/250,681, filed Nov. 30, 2000; Ser. No. 60/250,683, filed Nov. 30, 2000; and Ser. No. 60/267,639, filed Feb. 10, 2001.

This application also incorporates by reference the following publications: Richard P. Haugland, *Handbook of Fluorescent Probes and Research Chemicals* ($6^{th}$ ed. 1996); Joseph R. Lakowicz, *Principles of Fluorescence Spectroscopy* ($2^{nd}$ Edition 1999); and Bob Sinclair, *Everything's Great When It Sits on a Chip: A Bright Future for DNA Arrays*, 13 THE SCIENTIST, May 24, 1999, at 18.

FIELD OF THE INVENTION

The invention relates to assays for molecular modifications. More particularly, the invention relates to assays for detecting molecular modifications such as phosphate modifications and the presence and/or activity of enzymes and other agents involved in facilitating or otherwise regulating such modifications.

BACKGROUND OF THE INVENTION

The physiological modification of molecules and supramolecular assemblies plays a major role in the structure and regulation of biological systems. These modifications may include phosphorylation, cyclization, glycosylation, acylation, and/or sulfation, among others, and the modified molecules may include polypeptides, nucleic acids, and/or lipids, among others. The importance of modifications is particularly evident in the cell-signaling pathway, in which extracellular and intracellular substances related by phosphate modifications such as phosphorylation and cyclization influence the position, nature, and activity of cells.

FIG. 1 is a schematic view of a representative cell-signaling pathway 100. Here, signaling cells 102 produce signal substances 104a,b that interact with target cells 106 to effect a response in the target cells. These responses may be short term, such as glycogen breakdown or muscle contraction, among others. These responses also may be long term, such as growth, differentiation, reproduction, and/or apoptosis, among others. Generally, these responses are brought about by increasing, decreasing, and/or maintaining enzyme activity in the target cells.

Signaling cells 102 are cells capable of producing a signal (substance) that can effect a specific response in another (target) cell. The signaling cells may be components of an endocrine, paracrine, or nervous system. The endocrine system is an organism-wide control system that regulates body function using hormones released by endocrine organs into the bloodstream. The endocrine organs include the pituitary gland, thyroid gland, parathyroid glands, adrenal glands, thymus gland, pineal body, pancreas, ovaries, testes, and kidneys. The paracrine system is a local control system that regulates nearby cells using local mediators released into the extracellular medium. The nervous system is a specialized control system that regulates specific cells using electrical impulses and neurotransmitters.

Signal substances 104a,b are substances through which a signaling cell may communicate with target cells, evoking a specific response. Signal substances may act as hormones, local mediators, and/or neurotransmitters, among others. Signal substances may take the form of proteins, small peptides, amino acids, nucleotides, steroids (e.g., cortisol, steroid sex hormones, vitamin D), retinoids, fatty acid derivatives, and dissolved gases (e.g., nitric oxide (NO) and carbon monoxide (CO)), among others.

Target cells 106 are cells capable of responding to a specific signal substance produced by a signaling cell. The ability to respond may depend on the cell and on the signal substance. For example, the signal substance thyroxine from the thyroid gland may evoke a response in nearly all cells, whereas the signal substance progesterone from the ovary may evoke a response only in specific cells in the lining of the uterus. The target response may include kinase activity, GTP binding, and/or cyclic nucleotide production.

The ability of a cell to respond to a given signal substance generally is determined by whether the cell includes a receptor for the signal substance. Here, a receptor is any molecule or supramolecular assembly capable of specifically binding a signal substance and initiating a response in a target cell. Representative receptors include cell-surface receptors 110 located on the surface of the target cell and intracellular receptors 112 located within the cytosol 114 or nucleus 116 of the target cell.

The nature of the response initiated by binding of a signal substance is determined by the intracellular machinery to which the receptor is operatively coupled. For example, binding of the neurotransmitter acetylcholine to identical receptors in heart muscle cells and secretory cells causes muscle relaxation in the heart muscle cells and secretion in the secretory cells, due to differences in the associated intracellular machinery.

The remainder of this section examines (1) the receptor mechanisms that cells use to bind signal substances and to communicate this binding to the cell interior, (2) the intracellular pathways that cells use for regulation, (3) the effects of errors in cell-signaling pathways, and (4) selected shortcomings of current cell-signaling assays.

1. Receptor Mechanisms

Target cells generally have receptors capable of specifically binding specific signal substances, including cell-surface receptors and/or intracellular receptors, as described above. Cell-surface receptors are more common and include (A) G-protein-linked receptors, (B) enzyme-linked receptors, and (C) ion-channel-linked receptors. These receptors typically bind large and/or water-soluble signal substances, such as many peptide hormones. Intracellular receptors are less common and include (A) guanylyl cyclase and (B) ligand-activated gene regulatory proteins. These receptors typically bind small and/or water-insoluble signal substances, such as steroid hormones, thyroid hormones, retinoids, vitamin D, and NO.

FIG. 2 is a schematic view of a representative G-protein-linked cell-surface receptor mechanism 130 that includes a receptor protein 132, a G-protein 134, and a target protein 136. These proteins may be positioned on or within the plasma membrane 138 of a target cell. In use, a specific signal substance 140 binds to a signal-substance binding site 142 on the extracellular side 144 of the receptor protein and thereby creates, exposes, or otherwise activates (*) a G-protein binding site 146 on the intracellular side 148 of the receptor protein. The G-protein then binds to the G-protein binding site on the receptor protein and thereby creates, exposes, or otherwise activates (*) a target-protein binding site 150 on the G-protein. The G-protein then dissociates from the receptor protein, binds (via the target-protein binding site) to the target protein, and activates (*) the target protein. Activation and deactivation of the G-protein may involve binding of a guanosine triphosphate (GTP) molecule and dephosphorylation of the GTP molecule, respectively. The receptor protein may belong to a large superfamily of homologous, seven-pass transmembrane proteins. These seven-pass proteins consist of a single polypeptide chain that crosses the membrane seven times, with an extracellular signal-substance binding portion and an intracellular catalytic portion. The G-protein may be trimeric, consisting of three polypeptide chains—α, β, and γ—that associate and dissociate during signaling. The target protein may consist of an enzyme or ion channel, among others. In particular, the target protein may be an enzyme that modulates the presence or activity of second messengers within the cell. These second messengers (also known as intracellular messengers or intracellular mediators) may bind allosterically to specific cellular proteins to alter their conformation and hence their activity. These second messengers include adenosine 3',5'-cyclic monophosphate (cAMP) and calcium ($Ca^{2+}$).

In the cAMP pathway, the target protein may be adenylyl cyclase (also known as adenylate cyclase), and the G-protein may be a stimulatory G-protein ($G_s$) that activates the adenylyl cyclase to make cAMP, or an inhibitory G protein ($G_i$) that inhibits the adenylyl cyclase to prevent it from making cAMP. The cAMP produced by the adenylyl cyclase activates cAMP-dependent protein kinase (A-kinase), which is a serine/threonine kinase that in turn activates or inhibits other enzymes to effect a physiological response. For example, in connection with glycogen metabolism, A-kinase may inhibit glycogen synthase to shut down glycogen synthesis, and simultaneously activate phosphorylase kinase that in turn activates glycogen phosphorylase to break down glycogen. A variety of signal substances use cAMP as a second messenger, including calcitonin, chorionic gonadotropin, corticotropin, epinephrine, follicle-stimulating hormone, glucagon, luteinizing hormone, lipotropin, melanocyte-stimulating hormone, norepinephrine, parathyroid hormone (PTH), thyroid-stimulating hormone, and vasopressin. The level of cAMP may be reduced by phosphodiesterases (PDEs), and the activity of kinases may be reversed by phosphatases, as described below.

In the $Ca^{2+}$ pathway, the target protein may be a phospholipase with specificity for a phosphoinositide (i.e., inositol phospholipid), and the G-protein may be $G_q$, which activates the phospholipase to cleave the phosphoinositide to produce an intermediate that releases $Ca^{2+}$ from the endoplasmic reticulum. For example, the phospholipase phosphoinositide-specific phospholipase C (phospholipase C-β) cleaves the phosphoinositide phosphatidylinositol 4,5-bisphosphate ($PIP_2$) to produce the second messengers inositol triphosphate ($IP_3$) and diacylglycerol. The inositol triphosphate is water soluble and diffuses to the endoplasmic reticulum (ER), where it releases $Ca^{2+}$ from the ER by binding to $IP_3$-gated $Ca^{2+}$-release channels in the ER membrane. The diacylglycerol is membrane bound and may be cleaved to form the second messenger arachidonic acid or may activate the $Ca^{2+}$-dependent serine/threonine kinase protein kinase C that in turn activates or inhibits other enzymes to effect a response. A variety of signal substances use $Ca^{2+}$ as a second messenger, including acetylcholine, thrombin, and vasopressin.

FIG. 3 is a schematic view of a representative enzyme-linked cell-surface receptor mechanism 170 that includes a receptor protein 172 positioned across the plasma membrane 174 of a target cell. The receptor protein includes a signal-substance binding site 176 on the extracellular side 178 of the membrane and a catalytic portion 180 on the intracellular side 182 of the membrane. (In some cases, the catalytic portion of the receptor may be replaced or augmented by a separate enzyme directly associated with the receptor protein.) In use, a specific signal substance 184 binds to the signal-substance binding site, initiating a series of events (such as dimerization and concomitant autophosphorylation of the receptor proteins) that activates (*) the catalytic portion of the receptor. The receptor protein may belong to one of at least five classes of single-pass transmembrane proteins: (A) receptor guanylyl cyclases, which catalyze the production of guanosine 3',5'-cyclic monophosphate (cGMP) in the cytosol; (B) receptor tyrosine kinases, which phosphorylate specific tyrosine residues on some intracellular proteins, (C) tyrosine-kinase-associated receptors, which associate with proteins that phosphorylate specific tyrosine residues on some intracellular proteins; (D) receptor tyrosine phosphatases, which dephosphorylate specific tyrosine residues on some intracellular proteins, and (E) receptor serine/threonine kinases, which phosphorylate specific serine or threonine residues on some intracellular proteins. Some of these receptors are described below in more detail.

The signal substance also may bind to intracellular receptors, such as guanylyl cyclase. This enzyme produces cGMP from GTP, which then acts as a second messenger much like cAMP. As described above, cGMP also may be produced by enzyme-linked cell-surface receptors. cGMP is present in most tissues at levels $\frac{1}{10}$ to $\frac{1}{100}$ those of cAMP. A variety of compounds increase cGMP levels in cells, including (1) the hormones acetylcholine, insulin, and oxytocin, (2) the guanylate cyclase stimulators (and vasodilators) nitroprusside, nitroglycerin, sodium nitrate, and nitric oxide, (3) chemicals such as serotonin and histamine, and (4) peptides such as atrial natriuretic peptide (ANP) that relax smooth muscle.

The level of cyclic nucleotides such as cAMP and cGMP may be controlled by specialized enzymes known as phosphodiesterases (PDEs). These enzymes catalyze the hydrolysis of the 3'-ester bond of cAMP and/or cGMP to form the corresponding uncyclized nucleotide monophosphates AMP and GMP, respectively. More than 30 human PDEs are known, and there is great interest in the pharmaceutical industry in finding inhibitors for PDEs for a broad range of potential therapeutic applications. A selective inhibitor of PDE-5 has been commercialized as the drug Viagra™ (i.e., Sildenafil) for the treatment of male erectile dysfunction. Moreover, several PDE-4 inhibitors are in clinical trials as anti-inflammatory drugs for the treatment of diseases such as asthma 2. Intracellular Signaling Pathways Target cells may have intracellular signaling pathways capable of specifically binding signal substances, including cell-surface receptors and intracellular receptors, as described above. These pathways may include (1) a phosphorylation pathway involving ATP/ADP, and (2) a GTP-binding pathway involving GTP/GDP.

FIG. 4A is a schematic view of a representative portion of a phosphorylation pathway. Phosphorylation is the predominant mechanism used to regulate protein activity in eucaryotic cells. In phosphorylation, a phosphate group (P) is reversibly attached to the side chain of an amino acid in a protein. The attached phosphate group may cause structural changes in the protein, for example, due to electrostatic interactions between the negative charges on the phosphate group and positive charges on the side chains of nearby amino acids. These structural changes may affect the activity of the phosphorylated protein, enhancing or inhibiting its function.

Specialized enzymes control phosphorylation in cells. In particular, protein kinase enzymes transfer phosphate groups to proteins, and protein phosphatase enzymes remove phosphate groups from proteins. Protein kinases and protein phosphatases are found in great variety in eucaryotic cells: a single cell may contain more than 100 different kinases, and one percent of genes may code for kinases.

There are two major categories of protein kinases: (1) serine/threonine (S/T) kinases, and (2) tyrosine kinases. The S/T kinases function by selectively phosphorylating serine and threonine side chains on substrate proteins or peptides. These kinases include cyclic AMP-dependent kinase (A-kinase), cyclic GMP-dependent kinase (G-kinase), protein kinase C (C-kinase), $Ca^{2+}$-calmodulin-dependent kinase (CaM-kinase), phosphorylase kinase, MAP kinase, and TGF-β receptor, among others. The S/T kinases are predominantly cytosolic. The tyrosine kinases function by selectively phosphorylating tyrosine side chains on substrate proteins or peptides. These kinases include the receptor kinases for epidermal growth factor (EGF), platelet-derived growth factor (PDGF), fibroblast growth factors (FGFs), hepatocyte growth factor (HGF), insulin, insulinlike growth factor-1 (IGF-1), nerve growth factor (NGF), vascular endothelial growth factor (VEGF), and macrophage colony stimulating factor (M-CSF). These kinases also include the nonreceptor kinases associated with the tyrosine-kinase-associated receptors, such as the Src family (Src, Yes, Fgr, Fyn, Lck, Lyn, Hck, and Blk) and Janus family (JAK1, JAK2, and Tyk2) kinases. The tyrosine kinases are predominantly membrane bound. A few kinases function by selectively phosphorylating threonine and tyrosine side chains on substrate proteins or peptides. These kinases include the mitogen-activated protein (MAP) kinase-kinase.

FIG. 4B is a schematic of a representative portion of a GTP-binding pathway. The GTP-binding pathway generally resembles the phosphorylation pathway in that each pathway involves transfer of a phosphate group to a protein. However, in the GTP-binding pathway, the protein gains a phosphate group by exchanging a bound GDP for a bound GTP, whereas in the phosphorylation pathway, the protein gains a phosphate group by covalent addition of the phosphate group to a serine, threonine, or tyrosine by a kinase enzyme. The binding of a GTP to a GTP-binding protein may cause structural changes in the protein that in turn affect the activity of the protein. Examples of GTP-binding proteins include the trimeric G-proteins described above and the Ras superfamily of monomeric GTPases. The Ras proteins are activated by release of bound GDP and binding of GTP stimulated by guanine-nucleotide releasing proteins (GNRPs). The Ras proteins are inactivated by hydrolysis of the bound GTP by GTPase-activating proteins (GAPs).

FIG. 5 is a schematic view of a representative portion of a second messenger pathway that may follow the receptor activation shown in FIG. 4. Specifically, FIG. 5 shows the production of cyclic nucleotides by activated receptor cyclases such as adenylyl cyclase and guanylyl cyclase and the degradation of cyclic nucleotides to form the corresponding uncyclized nucleotide monophosphates by phosphodiesterases and/or other mechanisms.

A physiological response may require stimulation by only a single type of signal substance, or may require stimulation by two or more types of signal substances. The latter mechanism permits finer tuning of the physiological response through signal integration. For example, a protein may be activated only by phosphorylation by two different kinases, themselves activated by binding of two different signal substances to two different receptors. Alternatively, a protein may be activated only by concurrent phosphorylation and GTP binding, or by binding of two subunits whose binding is contingent on phosphorylation by separately activated kinases.

3. Effects of Errors

Errors in the signal transduction and regulation pathways described above can cause cancer and other diseases. Indeed, a primary cause of cancer is a mutation that makes a stimulatory gene product hyperactive, converting a proto-oncogene into an oncogene. The primary classes of known proto-oncogenes include the following cell-signaling proteins: (1) growth-factor receptors acting via tyrosine kinases, (2) GTP binding proteins, (3) membrane/cytoskeleton-associated tyrosine kinases, (4) cytoplasmic tyrosine kinases, (5) steroid-type growth-factor receptors, and (6) S/T kinases. Consequently, cell-signaling proteins have become important subjects of research and drug development.

4. Selected Shortcomings of Current Assays

Assays that determine the presence and/or activity of cell-signaling components are important tools in life sciences research, including high-throughput screening. Unfortunately, current assays have a number of shortcomings.

The presence and activity of kinases, for example, can be determined using assays capable of detecting phosphorylated amino acids. In a standard kinase assay, radioactive ATP and an appropriate protein substrate are added to a sample. If the sample includes kinases, radioactive phosphate groups will be transferred from the radioactive ATP to the protein substrate. The presence and activity of kinases can be determined by assaying the amount of radioactive protein substrate, for example, using heterogeneous methods such as a filter plate that involve separating the protein substrate and radioactive ATP, or homogeneous methods such as a scintillation proximity assay for detecting radioactive decay. Unfortunately, both approaches involve radioactivity, presenting a short-term safety hazard for the assay operator and a long-term storage and disposal problem.

In an alternative kinase assay, ATP, a luminescent protein, and an antibody against a phosphorylated form of the luminescent protein are added to a sample. If the sample includes kinases, the kinases will transfer phosphate groups from the ATP to the protein, the antibody will bind to the phosphorylated protein, and the luminescence polarization of the protein will increase (because its rotational mobility will decrease). Unfortunately, the binding of antibodies is very target specific, so that in general a different antibody will be needed for each substrate (depending on the sequence of the substrate, including whether a tyrosine, serine, or threonine is to be phosphorylated). This shortcoming is especially significant for serines and threonines. Thus, a different antibody may be needed for each of the many kinases, depending on the polypeptide sequences of the corresponding substrates. Yet, suitable antibodies may be unavailable for many substrates and kinases, especially for poorly studied or previously unstudied kinases, or take several months or more to prepare.

Significantly, assays for other cell-signaling components (such as phosphatases, phosphodiesterases, and/or cyclases) may have similar shortcomings, such as the use of radioactive reagents, if the assays exist at all. Moreover, these assays may have slow time courses and unstable endpoints that require precise timing of assay readouts. Thus, there is a need for improved assays for detecting enzyme activity, and in particular the presence and activity of cell-signaling components.

SUMMARY OF THE INVENTION

The invention provides assays for detecting molecular modifications such as phosphate modifications and the presence and/or activity of enzymes and other agents involved in facilitating or otherwise regulating such modifications.

DEFINITIONS

Figure 1:
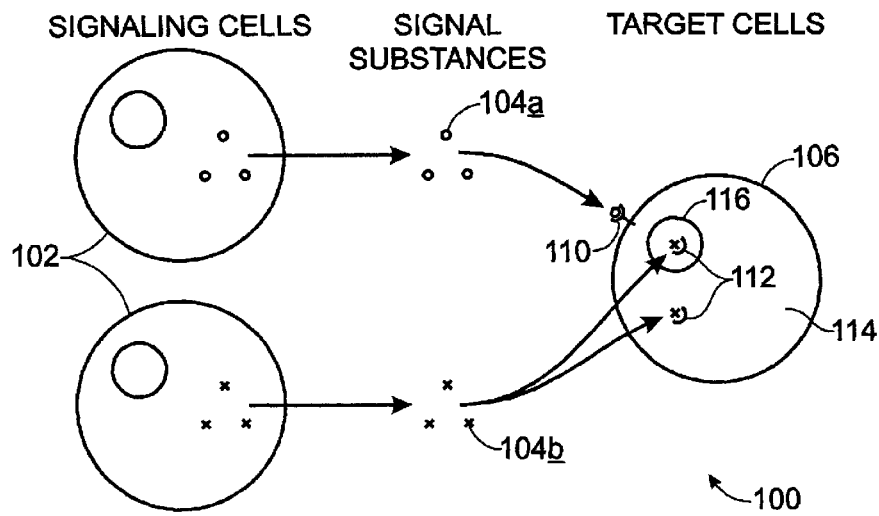
FIG. 1 is a schematic view of a cell-signaling pathway.
Figure 2:
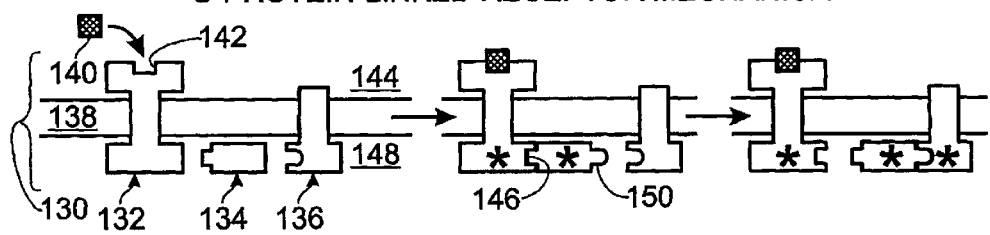
FIG. 2 is a schematic view of a G-protein-linked cell-surface receptor mechanism that includes a receptor protein, a G-protein, and a target protein, all associated with the plasma membrane of a target cell.
Figure 3:
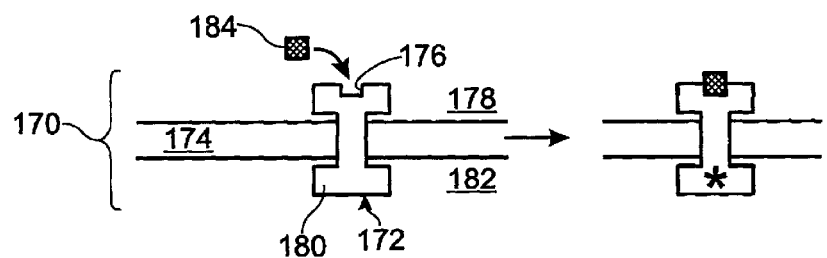
FIG. 3 is a schematic view of an enzyme-linked cell-surface receptor mechanism that includes a receptor protein positioned across the plasma membrane of a target cell.
Figure 4:
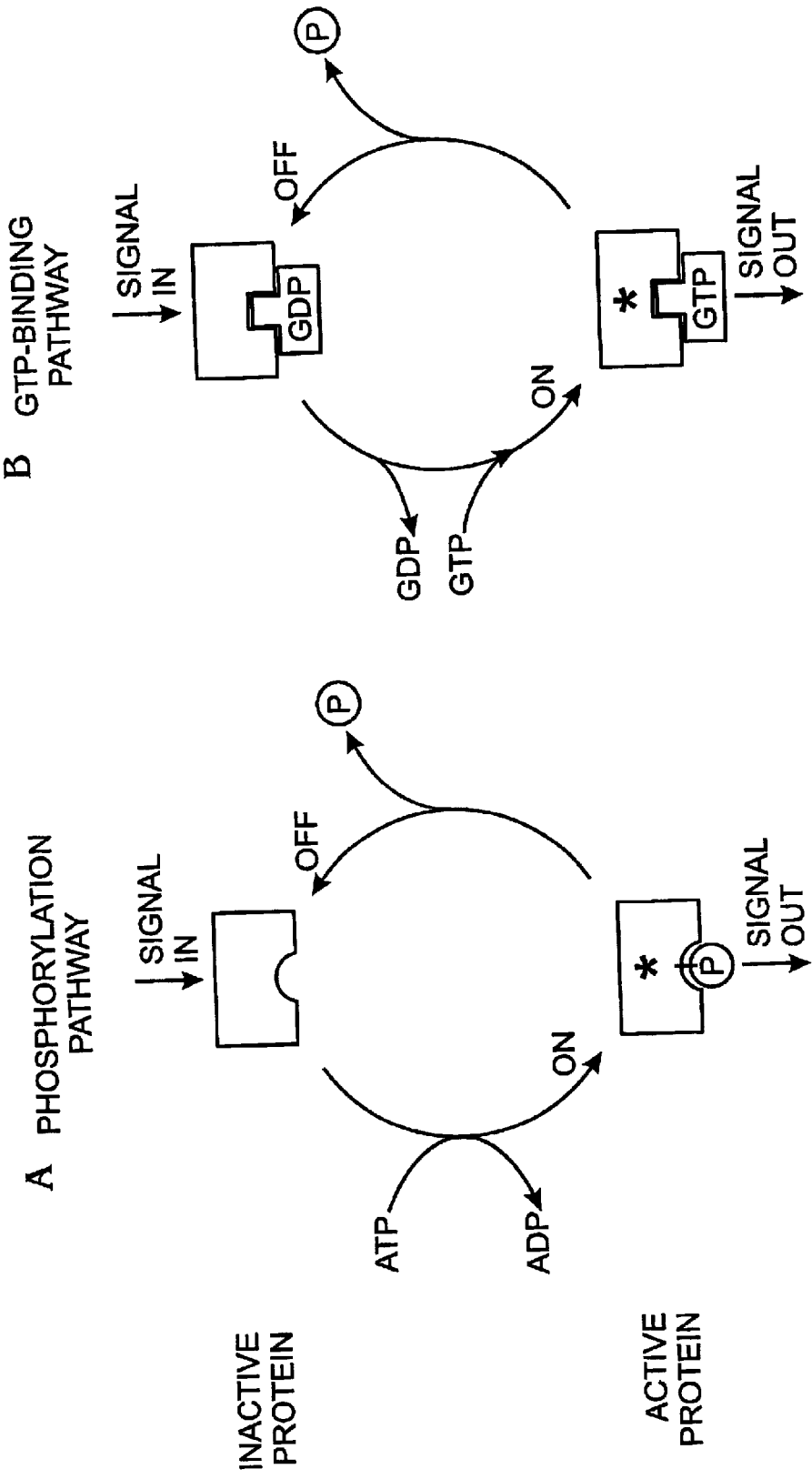
FIG. 4 is a schematic view of two common intracellular signaling pathways: (A) a phosphorylation pathway involving ATP/ADP, and (B) a GTP-binding pathway involving GTP/GDP.
Figure 5:
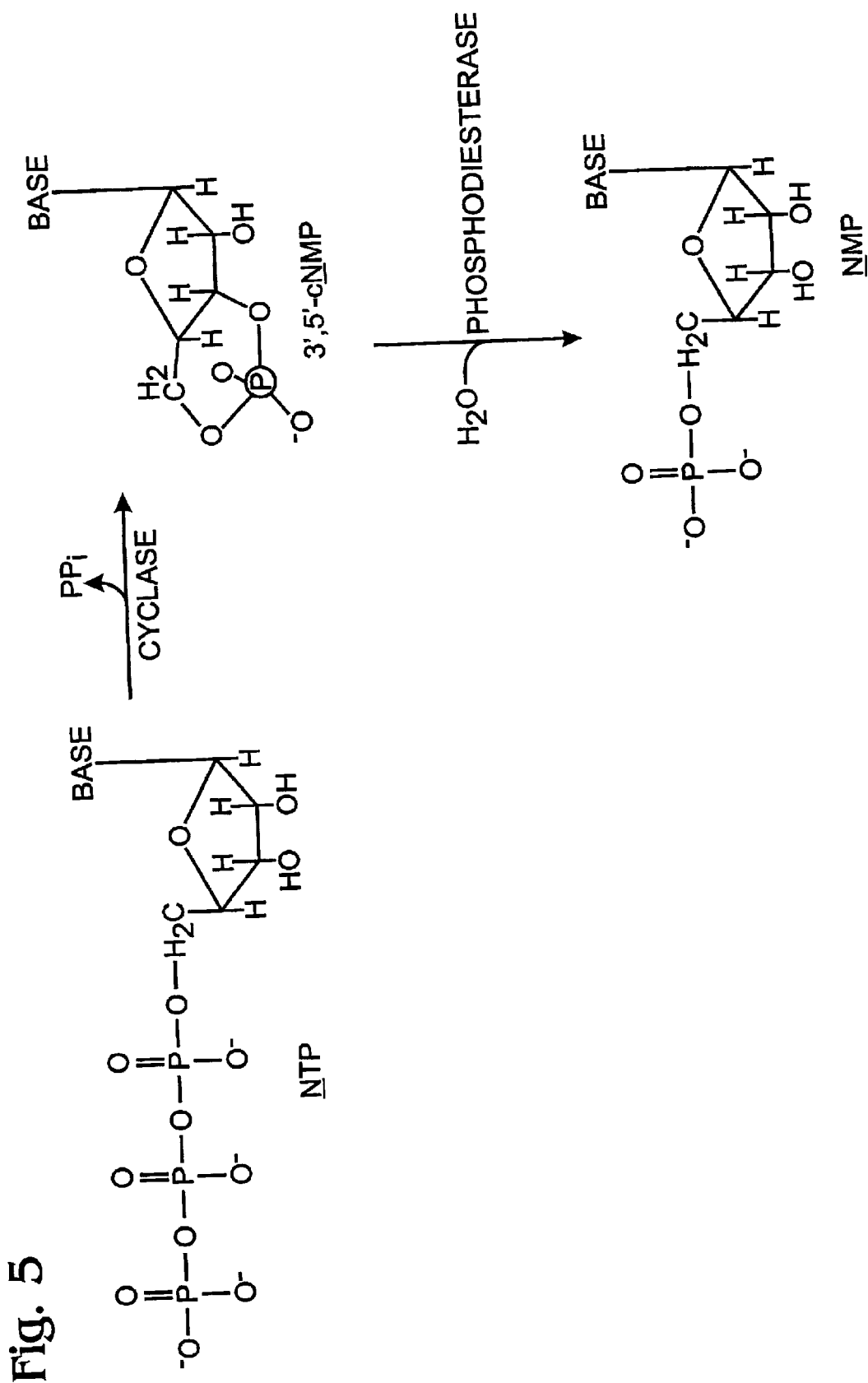
FIG. 5 is a schematic view of a representative portion of a second messenger pathway that may follow the receptor activation shown in FIG. 4.

The various technical terms used herein generally have the meanings that are commonly recognized by those skilled in the art. However, the following terms may have additional and/or alternative meanings, as described below:

Cyclization/decyclization—the formation or degradation of a ring connecting a phosphate group and a nucleoside in a nucleotide. A common cyclization forms cAMP and cGMP from ATP and GTP, respectively, by removing two phosphate groups from the nucleotide triphosphates and joining the "free" end of the remaining phosphate group to the sugar in the remaining nucleotide monophosphate. A common decyclization reaction degrades the ring to form AMP and GMP from cAMP and cGMP, respectively.

Immunoglobulin—a group of typically large glycoproteins secreted by plasma cells in vertebrates that function as antibodies in the immune response by binding to specific antigens.

Luminescent—capable of, suitable for, or exhibiting luminescence, which is the emission of light by sources other than a hot, incandescent body. Luminescence is caused by electronic transitions within a luminescent substance (or luminophore) from more energetic to less energetic states. Among several types are chemiluminescence, electrochemiluminescence, electroluminescence, photoluminescence, and triboluminescence, which are produced by chemical reactions, electrochemical reactions, electric discharges, absorption of light, and the rubbing or crushing of crystals, respectively. Molecules may be intrinsically and/or extrinsically luminescent, meaning that they are luminescent on their own or luminescent due to covalent and/or noncovalent association with another molecule that is luminescent. Exemplary luminescent molecules and mechanisms for producing luminescent molecules are described in U.S. patent application Ser. No. 09/815,932, filed Mar. 23, 2001, which is incorporated herein by reference.

Nucleotide—a compound comprising a nucleoside and a phosphate group, some of which function as cell regulators and some of which function as the basic constituent of DNA and RNA. A nucleoside in turn is a compound comprising a sugar, such as ribose or deoxyribose, and a purine or pyrimidine base, such as adenine, cytosine, guanine, thymine, or uracil. Nucleotides are named according to the identities of their constituent bases and sugars, the number of their constituent phosphates, and the presence or absence of cyclization. Suitable nucleotides are listed in the following table:

| Nucleotide | Abbreviation |
|---|---|
| Adenosine cyclic monophosphate | cAMP |
| Cytidine cyclic monophosphate | cCMP |
| Guanosine cyclic monophosphate | cGMP |
| Thymidine cyclic monophosphate | cTMP |
| Uridine cyclic monophosphate | cUMP |
| Adenosine monophosphate | AMP |
| Cytidine monophosphate | CMP |
| Guanosine monophosphate | GMP |
| Thymidine monophosphate | TMP |
| Uridine monophosphate | UMP |

Phosphorylation/dephosphorylation—the introduction or removal of a phosphate group to or from an organic molecule such as a polypeptide. Phosphorylation is a versatile posttranslational modification that is a recurrent theme for regulation of enzyme activity and signal transduction pathways.

Polypeptide—a polymer comprising two or more amino acid residues linked together by covalent bonds, typically from amino end to carboxyl end by peptide bonds, and modifications and complexes thereof. Polypeptides generally include peptides and/or proteins, among others. Here, peptide generally refers to smaller polypeptides (e.g., less than about 100, 50, 20, or 10 amino acids, among others), and protein generally refers to larger polypeptides, and complexes thereof, possibly modified by other organic or inorganic conjugated chemical groups, such as phosphates, sugars, and so on. Polypeptides may include straight chains and/or branched chains, among others. Suitable amino acids are listed in the following table:

| Amino acid | Three-letter abbreviation | One-letter abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | B |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Specific binding—binding to a specific binding partner to the exclusion of binding to most other moieties. Specific binding can be characterized by a binding coefficient. Generally, specific binding coefficients range from $10^{-4}$ M to $10^{-12}$ M and lower, and preferred specific binding coefficients range from $10^{-8}$ or $10^{-9}$ M to $10^{-12}$ M and lower.

DETAILED DESCRIPTION

The invention provides assays for detecting molecular modifications and the presence and/or activity of enzymes and other agents involved in facilitating or otherwise regulating such modifications. The modifications may include among others phosphate modifications, such as the phosphorylation and dephosphorylation of molecules such as polypeptides and the cyclization and decyclization of molecules such as nucleotides. The enzymes may include among others enzymes involved in performing and/or regulating phosphorylation, dephosphorylation, cyclization, and decyclization modifications, such as kinases, phosphatases, cyclases, and phosphodiesterases (PDEs), respectively. The assays may include among others luminescence assays, such as luminescence polarization, luminescence resonance energy transfer, and/or luminescence intensity. The assays provided by the invention may be useful in a variety of applications, including without limitation life science research, drug research, accelerated drug discovery, assay development, and high-throughput screening, among others.

1. Overview

Figure 6:
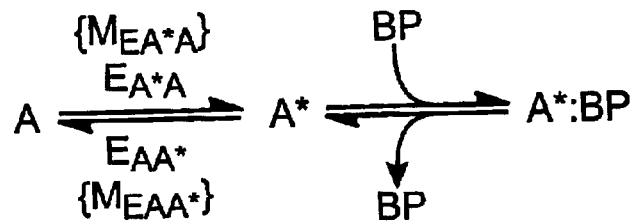
FIG. 6 is a schematic view of species and/or reactions that may be analyzed using assays provided by the invention.

FIG. 6 shows species and/or reactions that may be analyzed using assays provided by the invention. The species include reactant and product A and A*, respectively, enzymes $E_{AA*}$ and $E_{A*A}$, and/or enzyme modulators $M_{EAA*}$ and $M_{EA*A}$, among others. The assays may be used to analyze the presence and/or quantity of A and/or A*. Alternatively, or in addition, the assays may be used to analyze the presence and/or activity of $E_{AA*}$, $E_{A*A}$, $M_{EAA*}$, and/or $M_{EA*A}$. Quantity refers generally to amount, which may be defined intrinsically and/or extrinsically, for example, using concentration and/or number or mass, respectively. Activity refers generally to rate, which may be defined as the rate of substrate consumption and/or product formation per time. Here, quantity and/or amount may be used so as to encompass the simple presence of components, and activity and/or rate may be used so as to encompass the simple presence of activity.

A and A* generally comprise any two species related by a modification (denoted by the presence or absence of *). A and A* may include molecules and assemblies of molecules such as polypeptides and/or nucleotides, among others. The modification may include phosphate modifications such as phosphorylation, dephosphorylation, cyclization, and/or decyclization, among others, and nonphosphate modifications such as nonphosphate posttranslational modifications of polypeptides, among others. A and A* may be related as substrate and product in a reaction, such as an enzyme-catalyzed reaction. Thus, depending on the direction of the reaction, A and A* in a phosphate modification may be a phosphorylated polypeptide, a nonphosphorylated polypeptide, a cyclized nucleotide, or a noncyclized nucleotide, among others. In some embodiments, A and/or A* may include components intended to facilitate detection of binding between A or A* and BP, such as a luminophore, a quencher, an energy transfer partner, and the like.

BP generally comprises any binding partner capable of binding specifically to A or A* (i.e., the modified species or the unmodified species) but not to both. BP may include any binding partner having the specified binding properties that does not include a polypeptide and/or an immunoglobulin, and/or a functional portion or fragment thereof. Alternatively, or in addition, BP may include one or more metal ions, including dicationic, tricationic, and polycationic metal ions, among others. Suitable dicationic metal ions include iridium ($Ir^{2+}$), osmium ($OS^{2+}$), platinum ($Pt^{2+}$), rhenium ($Re^{2+}$), and ruthenium ($Ru^{2+}$), among others. Suitable tricationic metal ions include including aluminum ($Al^{3+}$), chromium ($Cr^{3+}$), iron ($Fe^{3+}$), gallium ($Ga^{3+}$), manganese ($Mn^{3+}$), scandium ($Sc^{3+}$), titanium ($Ti^{3+}$), vanadium ($V^{3+}$), and/or yttrium ($Y^{3+}$), among others. Preferred metal ions include aluminum, iron, and gallium. The metal ions may interact with or otherwise be involved in or required for binding with the modification on A or A*, such as the phosphate group on a phosphorylated protein or a noncyclized nucleotide. Alternatively, or in addition, BP may include one or more charged portions to facilitate or otherwise participate in the binding reaction with A or A*, particularly charged portions that are immobilized relative to BP. Alternatively, or in addition, BP may bind to a substrate such as A or A* only if it is phosphorylated, where the binding between the substrate and the binding partner is substantially nonspecific with respect to the structure of the substrate aside from any phosphate groups. Thus, the binding may occur substantially without regard to the target amino acid or surrounding amino acid sequence in a phosphorylation/dephosphorylation assay, or the base or nucleoside in a cyclization/decyclization assay. Alternatively, or in addition, BP may include a macromolecule and/or a particle. Here, particles include nanoparticles and microparticles, among others, where nanoparticles are particles with at least one dimension less than about 100 nm, and microparticles are particles with dimensions between about 100 nm and about 10 μm. Alternatively, or in addition, BP may be linked to an associated solid phase, such as a bead, membrane, or sample holder, among others. The link may be formed using any suitable mechanism, including hydrogen bonding, ionic bonding, electrostatic binding, hydrophobic interactions, Van der Waals interactions, and/or covalent attachment, among others. In some embodiments, BP may include components intended to facilitate detection of binding between BP and A or A*, such as a luminophore, a quencher, an energy transfer partner, and the like.

$E_{AA^*}$ and $E_{A^*A}$ generally comprise any enzymes or other catalysts capable of facilitating reactions converting A to A* and A* to A, respectively. $E_{AA^*}$ and $E_{A^*A}$ may include among others enzymes such as kinases and phosphatases, which catalyze the addition and removal of phosphate groups to and from polypeptides, respectively. $E_{AA^*}$ and $E_{A^*A}$ also may include enzymes such as cyclases and phosphodiesterases, which catalyze the cyclization and decyclization of nucleotides, respectively.

$M_{EAA^*}$ and $M_{EA^*A}$ generally comprise any modulators or other agents capable of modulating or otherwise affecting the activity of $E_{AA^*}$ and $E_{A^*A}$, respectively. The modulator may be a change in environmental condition, such as a change in sample temperature, but more typically is an enzyme or other reagent added to the sample. The modulator may be a chemical reagent, such as an acid, base, metal ion, organic solvent, and/or other substance intended to effect a chemical change in the sample. Alternatively, or in addition, the modulator may have or be suspected to have a biological activity or type of interaction with a given biomolecule, such as an enzyme, drug, oligonucleotide, nucleic acid polymer, peptide, protein, and/or other biologically active molecule. The modulator may include an agonist or inhibitor capable of promoting or inhibiting, respectively, the activity of the modulated enzyme. For example, in a cyclic nucleotide assay, preferred agonists include forskolin and isoproterenol, and preferred inhibitors include propranolol and Zaprinast.

2. Assays

Figure 7:
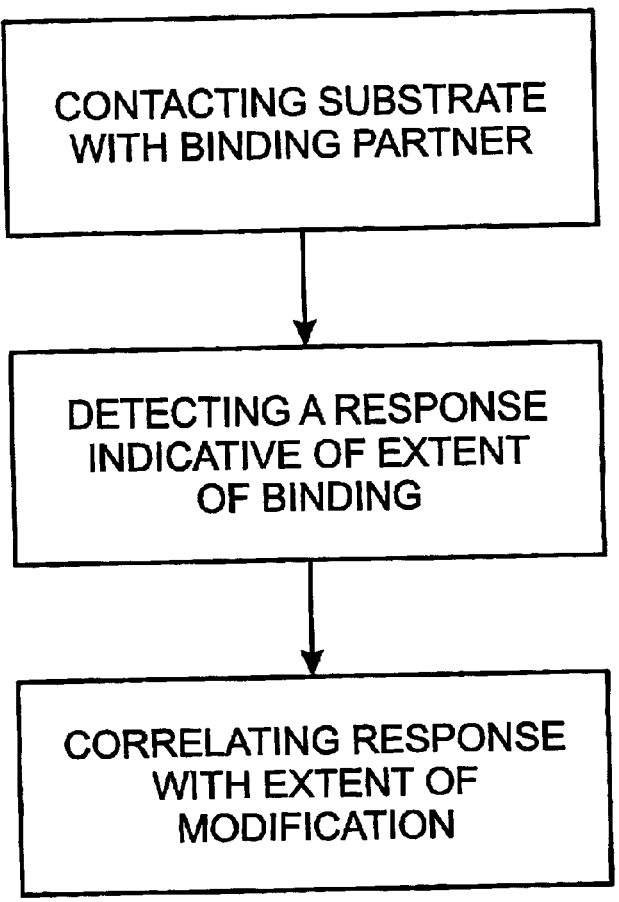
FIG. 7 is a flowchart showing steps that may be used alone, together, or in combination with other steps to construct assays according to various aspects of the invention.

FIG. 7 shows several steps that may be used alone, together, or in combination with other steps to construct assays according to various aspects of the invention. These steps may include (1) contacting at least one member of a pair of molecules or other entities related by a modification as described above with a binding partner capable of binding one of the pair of molecules but not the other as described above, (2) detecting a response indicative of the extent of binding between the at least one member of the pair and the binding partner, and (3) correlating the response with the extent of modification, or with the presence and/or activity of an enzyme that affects the modification. The assays further may include contacting the at least one member with the enzyme before and/or after the steps of contacting, detecting, and correlating. The assays further may include contacting the at least one member and the enzyme with a candidate compound such as a putative modulator before and/or after the step of contacting the at least one member with the enzyme, and determining the ability of the candidate compound to promote or inhibit the modification by its effects on the extent of binding. Alternatively, or in addition, the assays further may include washing the sample including the at least one member and the binding partner to remove any member of the pair not bound to the binding partner prior to the step of detecting the extent of binding. In some embodiments, the assays may include repeating the steps of contacting, detecting, and/or correlating for the same sample and/or a plurality of different samples. For example, the assays may involve providing a sample holder having a plurality of sample sites supporting a corresponding plurality of samples, and sequentially and/or simultaneously repeating the steps of contacting, detecting, and/or correlating for the plurality of samples. The remainder of this section describes in more detail the steps of (1) contacting, (2) detecting, and (3) correlating.

1. Contacting

The step of contacting assay components such as enzymes, enzyme modulators, substrates, products, and/or binding partners with one another and/or with other species generally comprises any method for bringing any specified combination of these components into functional and/or reactive contact. A preferred method is by mixing and/or forming the materials in solution, although other methods, such as attaching one or more components such as the binding partner to a bead or surface, also may be used, as long as the components retain at least some function, specificity, and/or binding affinity following such attachment. Exemplary apparatus having fluidics capability suitable for contacting or otherwise preparing assay components are described in the following patent applications, which are incorporated herein by reference: U.S. patent application Ser. No. 09/777,343, filed Feb. 5, 2001; and U.S. Provisional Patent Application Ser. No. 60/267,639, filed Feb. 10, 2001.

One of more of the assay components may comprise a sample, which typically takes the form of a solution containing one or more biomolecules that are biological and/or synthetic in origin. The sample may be a biological sample that is prepared from a blood sample, a urine sample, a swipe, or a smear, among others. Alternatively, the sample may be an environmental sample that is prepared from an air sample, a water sample, or a soil sample, among others. The sample typically is aqueous but may contain biologically compatible organic solvents, buffering agents, inorganic salts, and/or other components known in the art for assay solutions.

The assay components and/or sample may be supported for contact and/or analysis by any substrate or material capable of providing such support. Suitable substrates may include microplates, PCR plates, biochips, and hybridization chambers, among others, where features such as microplate wells and microarray (i.e., biochip) sites may comprise assay sites. Suitable microplates are described in the following U.S. patent applications, which are incorporated herein by reference: Ser. No. 08/840,553, filed Apr. 14, 1997; and Ser. No. 09/478,819, filed Jan. 5, 2000. These microplates may include 96, 384, 1536, or other numbers of wells. These microplates also may include wells having small ($\leq 50$ μL) volumes, elevated bottoms, and/or frustoconical shapes capable of matching a sensed volume. Suitable PCR plates may include the same (or a similar) footprint, well spacing, and well shape as the preferred microplates, while possessing stiffness adequate for automated handling and thermal stability adequate for PCR. Suitable microarrays include nucleic acid and polypeptide microarrays, which are described in Bob Sinclair, *Everything's Great When It Sits on a Chip: A Bright Future for DNA Arrays*, 13 THE SCIENTIST, May 24, 1999, at 18, which is incorporated herein by reference: Suitable hybridization chambers are described in PCT Patent Application Ser. No. PCT/US99/03678, filed Feb. 19, 1999, which is incorporated herein by reference.

2. Detecting

The step of detecting a response indicative of the extent of binding generally comprises any method for effectuating such detection, including detecting and/or quantifying a change in, or an occurrence of, a suitable parameter and/or signal. The method may include luminescence and/or nonluminescence methods, and heterogeneous and/or homogeneous methods, among others.

Luminescence and nonluminescence methods may be distinguished by whether they involve detection of light emitted by a component of the sample. Luminescence assays involve detecting light emitted by a luminescent compound (or luminophore) and using properties of that light to understand properties of the compound and its environment. A typical luminescence assay may involve (1) exposing a sample to a condition capable of inducing luminescence from the sample, and (2) measuring a detectable luminescence response indicative of the extent of binding between the member of interest and a corresponding binding partner. Most luminescence assays are based on photoluminescence, which is luminescence emitted in response to absorption of suitable excitation light. However, luminescence assays also may be based on chemiluminescence, which is luminescence emitted in response to chemical excitation, and electrochemiluminescence, which is luminescence emitted in response to electrochemical energy. Suitable luminescence assays include, among others, (1) luminescence intensity, which involves detection of the intensity of luminescence, (2) luminescence polarization, which involves detection of the polarization of light emitted in response to excitation by polarized light, and (3) luminescence energy transfer, which involves detection of energy transfer between a luminescent donor and a suitable acceptor. These and other luminescence assays are described below in Example 14 and materials cited therein. Nonluminescence assays involve using a detectable response other than light emitted by the sample, such as absorption, scattering, and/or radioactivity, among others. These and other nonluminescence assays are described in the following materials, which are incorporated herein by reference: U.S. patent application Ser. No. 09/765,869, filed Jan. 19, 2001; and Joseph R. Lakowicz, *Principles of Fluorescence Spectroscopy* ($2^{nd}$ ed. 1999).

The detectable luminescence response generally comprises a change in, or an occurrence of, a luminescence signal that is detectable by direct visual observation and/or by suitable instrumentation. Typically, the detectable response is a change in a property of the luminescence, such as a change in the intensity, polarization, energy transfer, lifetime, and/or excitation or emission wavelength distribution of the luminescence. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence assays, the detectable response may be generated directly using a luminophore associated with an assay component actually involved in binding such as A* or BP, or indirectly using a luminophore associated with another (e.g., reporter or indicator) component. Suitable methods and luminophores for luminescently labeling assay components are described in the following materials, which are incorporated herein by reference: Richard P. Haugland, *Handbook of Fluorescent Probes and Research Chemicals* ($6^{th}$ ed. 1996); U.S. patent application Ser. No. 09/813,107, filed Mar. 19, 2001; and U.S. patent application Ser. No. 09/815,932, filed Mar. 23, 2001.

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a tricationic metal ion or other suitable binding partner. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a luminescence response that is affected in some way by binding or unbinding of bound and unbound species without separating the bound and unbound species. Homogeneous assays typically are simpler to perform but more complicated to develop than heterogeneous assays.

3. Correlating

The step of correlating generally comprises any method for correlating the extent of binding with the extent of modification of the assay component being analyzed, and/or with the presence and/or activity of an enzyme that affects the modification. The nature of this step depends in part on whether the detectable response is simply detected or whether it is quantified. If the response is simply detected, it typically will be used to evaluate the presence of a component such as a substrate, product, and/or enzyme, or the presence of an activity such as an enzyme or modulator activity. In contrast, if the response is quantified, it typically will be used to evaluate the presence and/or quantity of a component such as a substrate, product, and/or enzyme, or the presence and/or activity of a component such as an enzyme or modulator.

The correlation generally may be performed by comparing the presence and/or magnitude of the response to another response (e.g., derived from a similar measurement of the same sample at a different time and/or another sample at any time) and/or a calibration standard (e.g., derived from a calibration curve, a calculation of an expected response, and/or a luminescent reference material). Thus, for example, in a polarization assay for cyclic nucleotide concentration, the cyclic nucleotide concentration in an unknown sample may be determined by matching the polarization measured for the unknown with the cyclic nucleotide concentration corresponding to that polarization in a calibration curve generated under similar conditions by measuring polarization as a function of cyclic nucleotide concentration. More generally, the following table shows representative qualitative changes in the indicated detectable luminescence response upon binding between A* and BP following a forward reaction A→A*.

| Label on A* | Label on BP | Intensity (Luminophore) | Intensity (Acceptor) | FP (Luminophore) | ET (Lum. → Acc.) |
|---|---|---|---|---|---|
| Luminophore | — | | | Increases | |
| — | Luminophore | | | Increases | |
| Luminophore | Quencher | Decreases | | | |
| Quencher | Luminophore | Decreases | | | |
| Luminophore | Acceptor | Decreases | Increases | Decreases | Increases |
| Acceptor | Luminophore | Decreases | Increases | | Increases |

This reaction is representative of a phosphorylation reaction performed by a kinase or a decyclization reaction performed by a PDE, assuming that the binding partner binds to the (noncyclized) phosphorylated species. Similarly, the following table shows representative qualitative changes in the indicated detectable luminescence response upon binding of A* and BP following the reverse reaction A*→A.

| Label on A* | Label on BP | Intensity (Luminophore) | Intensity (Acceptor) | FP (Luminophore) | ET (Lum. → Acc.) |
|---|---|---|---|---|---|
| Luminophore | — | | | Decreases | |
| — | Luminophore | | | Decreases | |
| Luminophore | Quencher | Increases | | | |
| Quencher | Luminophore | Increases | | | |
| Luminophore | Acceptor | Increases | Decreases | Increases | Decreases |
| Acceptor | Luminophore | Increases | Decreases | | Decreases |

This reaction is representative of a dephosphorylation reaction performed by a phosphatase or a cyclization reaction performed by a cyclase, assuming again that the binding partner binds to the (noncyclized) phosphorylated species.

3. EXAMPLES

The following examples describe without limitation further aspects of the invention. These aspects include (1) the ability of binding partners such as tricationic metal ions to bind specifically to phosphorylated species such as phosphopeptides and nucleotides, and (2) the use of such binding in assays for enzymes and other agents involved in phosphorylation and dephosphorylation (e.g., kinases and phosphatases, respectively) and cyclization and decyclization (e.g., cyclases and PDEs, respectively), among others. These aspects are applicable to a wide variety of enzymes and enzyme substrates and products.

Example 1

This example describes a macromolecular trapping system for use in luminescence polarization and/or energy transfer assays, among others, in accordance with aspects of the invention. In this system, $Ru^{2+}$ is entrapped in small (~20–30 kDa) synthetic polymer macromolecules (MM), which are obtained from PreSens Precision Sensing (Neuburg/Donau, Germany). These macromolecules are relatively hydrophilic, with carboxyl groups on their surfaces for activation. The MM with the entrapped $Ru^{2+}$ is used as a support to immobilize tricationic metal cations, including $Fe^{3+}$ and $Ga^{3+}$. Specifically, the chelator imidodiacetic (IDA) acid is linked to the MM using the secondary amine group of IDA and a carboxyl group on the MM. Afterwards, the MM-IDA is incubated with either $FeCl_3$ or $GaCl_3$. The $FeCl_3$ quenches the luminescence of $Ru^{2+}$, whereas the $GaCl_3$ does not. The macromolecule loaded with $Fe^{3+}$ or $Ga^{3+}$ is denoted MM-Fe or MM-Ga, respectively.

The macromolecular trapping system may be used in a variety of kinase, phosphatase, phosphodiesterase, and/or cyclase assays, as described below in Examples 3–5 and 7–9. In an exemplary assay, a kinase enzyme phosphorylates a luminescently labeled kinase substrate, which binds to the metal cations immobilized on the MM. Binding is detected using polarization and/or energy transfer methods, among others, for example, using apparatus and methods as described herein. Binding is detectable using polarization because binding leads to a decrease in substrate mobility and a concomitant increase in the polarization of light emitted by luminophores bound to the substrate. Similarly, binding is detectable using energy transfer because binding leads to a decrease in separation between the luminophores bound to the substrate and the $Ru^{2+}$ immobilized in the MM, and a concomitant increase in energy transfer from the $Ru^{2+}$ (donor) to the luminophore (acceptor).

This approach may be extended by various modifications and/or substitutions. For example, in polarization assays, the $Ru^{2+}$ may be omitted, if desired. In energy transfer assays, the $Ru^{2+}$ may be replaced by any energy transfer partner, as long as the energy transfer partner supported by the MM is capable of energy transfer to or from a complementary energy transfer partner supported by the species binding to the MM. Exemplary energy transfer partners are described in U.S. patent application Ser. No. 09/815,932, filed Mar. 23, 2001, which is incorporated herein by reference. Also, the $Ru^{2+}$ or its analog does not need to be encapsulated in the MM. A luminescent species may be attached directly to a suitable $Fe^{3+}$ or $Ga^{3+}$ chelate. In a heterogeneous assay, phosphorylated proteins bound via $Ga^{3+}$ or $Fe^{3+}$ to microplates, particles, or inner surfaces of microfluidic devices may be detected after a wash by measuring luminescence intensity. Such detection can take place either directly on the surfaces or in the solution phase by adding an elution solution such as a phosphate buffer. With other detection methods, such as the laser-scanning method used in fluorometric microvolume assay technology (FMAT™) technology (PE Biosystems, Foster City, Calif.), the bound phosphoproteins can be detected directly on the beads, without the need for washing or separation. Other labels such as enzymes also may be used in the heterogeneous format.

Potential difficulties with this system include (1) interference from compounds (e.g., ATP, free phosphate, EDTA, and possibly primary/secondary amines) that may compete with or otherwise affect the interaction between the metal and the phosphorylated protein, and (2) difficulty in maintaining a pH that preserves the affinity and selectivity of the binding between the metal and phosphorylated protein.

Example 2

This example describes assays for the presence, activity, substrates, and/or products of kinases in accordance with aspects of the invention. Similar assays may be used to analyze phosphatases in which the substrates and products of the kinase reaction become the products and substrates of the phosphatase reaction, respectively.

Kinases catalyze the addition of phosphate groups to appropriate substrates, as shown below:

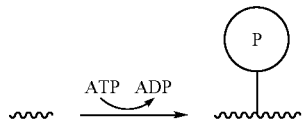

Thus, the presence and/or activity of a kinase may be detected by a decrease in the concentration of a nonphosphorylated (e.g., polypeptide) substrate and/or by an increase in the concentration of a corresponding phosphorylated product, among others. (The presence and/or activity of a phosphatase may be detected similarly by a decrease in the concentration of a phosphorylated substrate and/or an increase in the concentration of a nonphosphorylated product.) The invention provides among others kinase assays that involve contacting a sample containing a candidate kinase (and optionally a modulator thereof) with a luminescently labeled nonphosphorylated polypeptide having at least one amino acid subject to phosphorylation (such as a tyrosine, serine, and/or threonine) and a binding partner that binds specifically to the phosphorylated polypeptide but not to the nonphosphorylated polypeptide. These assays further involve detecting a response indicative of the extent of binding between the polypeptide and the binding partner such as luminescence intensity, polarization, and/or energy transfer, and correlating the response with the extent of phosphorylation or nonphosphorylation of the polypeptide, and thus with the activity of the candidate kinase. The binding partner may include a metal ion such as a tricationic metal ion that interacts with the phosphate group on the phosphorylated polypeptide to facilitate the binding reaction. The binding partner also may include a macromolecule, a nanoparticle, a solid phase portion, a quencher, and/or an energy transfer partner complementary to the luminophore on the polypeptide, depending in part on the detection scheme.

Example 3

This example describes experiments to characterize binding between MM-Ga and a fluorescein-labeled di-phosphotyrosine 15-amino-acid peptide tracer denoted tyrosine kinase 1 (TK-1) tracer. These experiments show the utility of the MM-Ga system for detection of phosphorylated tyrosine and the presence and/or activity of tyrosine kinases and phosphatases.

Figure 8:
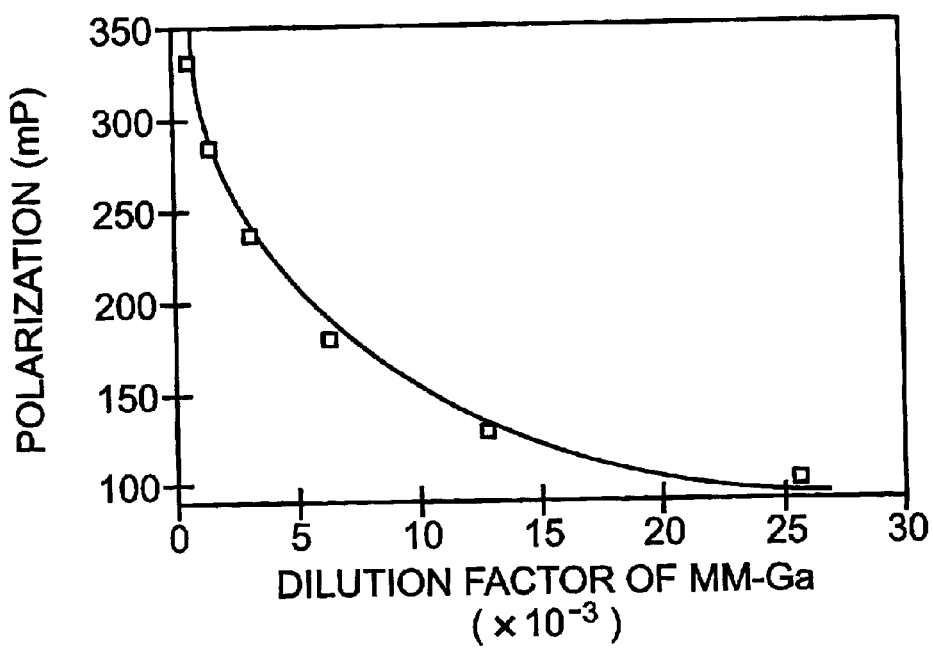
FIG. 8 is a graph showing the effects of incubating 10 nM TK-1 tracer with different concentrations of MM-Ga.

FIG. 8 shows the effects of incubating 10 nM TK-1 tracer with different concentrations of MM-GA (total volume=50 µL; incubation time=60 min). These experiments show that the maximum polarization change is more than 200 mP, at least when the MM-Ga and TK-1 tracer are incubated in MES buffer (0.1M MES, pH 5.5, 1.0 M NaCl). This polarization change is at least sufficient for most polarization assays.

Figure 9:
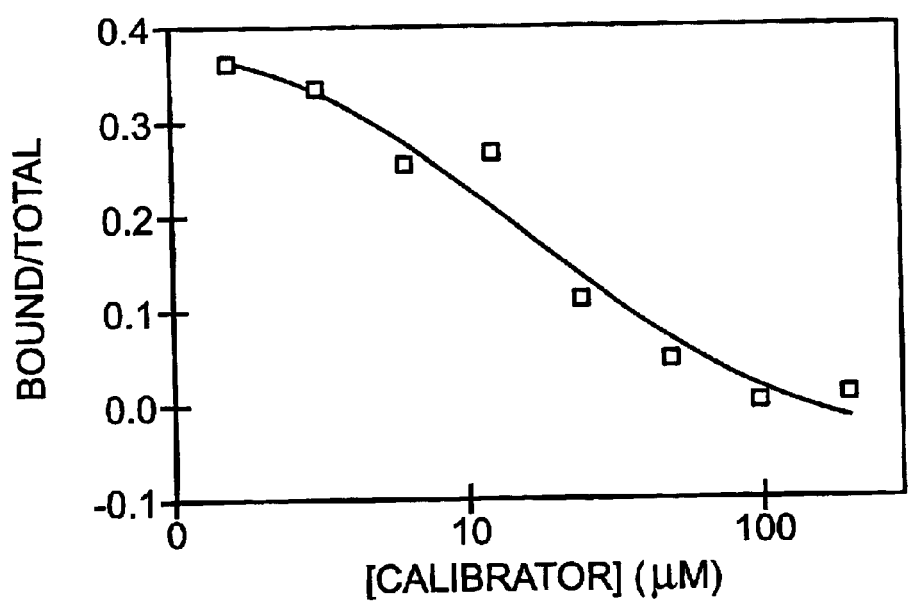
FIG. 9 is a graph showing a dose-response curve for TK-1 calibrator, with 10 nM TK-1 tracer and 1.6 nM (estimated) MM-Ga.

FIG. 9 shows a dose-response curve for TK-1 calibrator, with 10 nM TK-1 tracer and 1.6 nM (estimated) MM-Ga. The TK-1 calibrator is the same as the TK-1 tracer, without a fluorescein label. The bound/total ratio is calculated as in FIG. 8. These experiments show that the IC50 for the TK-1 calibrator also is around 10 µM. The IC50 (inhibitory concentration 50%) is the concentration of inhibitor required for 50% inhibition. More generally, the IC50 (or EC50 (effective concentration 50%)) is the drug concentration at which an associated response has decreased (increased) to 50% of the initial response, assuming that the response is a decreasing (increasing) function of drug concentration.

Example 4

This example describes experiments to characterize binding between MM-Ga and the following mono-seine fluorescein-labeled peptide tracer:

fluorescein-Leu-Arg-Arg-Ala-Ser-Leu-Gly (SEQ ID NO: 1)

This peptide is termed a "Kemptide," and the fluorescein-labeled peptide is termed a "fluo-Kemptide." These experiments use cAMP-dependent protein kinase A (PKA, Promega) as the enzyme and fluo-Kemptide as the substrate. These experiments show the utility of the MM-Ga system for detection of phosphorylated serine and the presence and/or activity of serine/threonine kinases and phosphatases.

Figure 10:
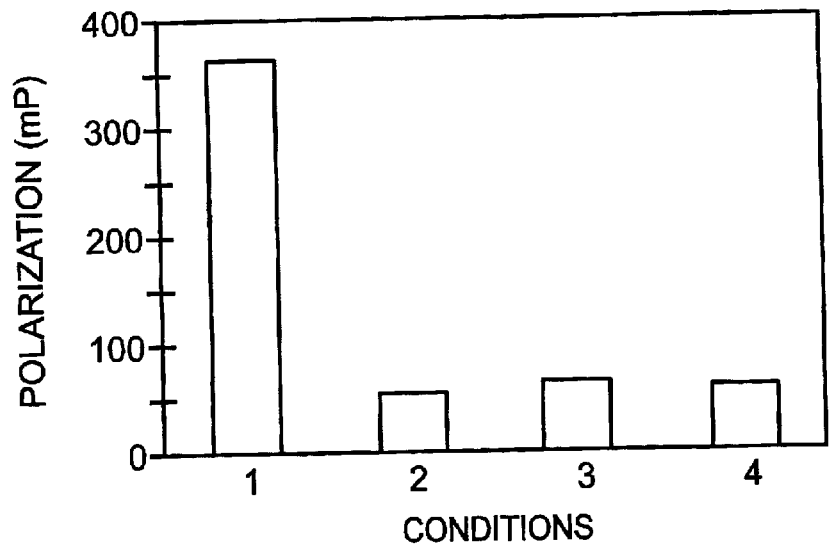
FIG. 10 is a bar graph showing results from an endpoint assay for PKA activity with MM-Ga under the following conditions: (1) reaction with enzyme, with MM-Ga; (2) reaction with enzyme, without MM-Ga; (3) reaction without enzyme, with MM-Ga; and (4) reaction without enzyme, without MM-Ga.

FIG. 10 shows an endpoint assay for PKA activity with MM-Ga under the following conditions: (1) reaction with enzyme, with MM-Ga; (2) reaction with enzyme, without MM-Ga; (3) reaction without enzyme, with MM-Ga; and (4) reaction without enzyme, without MM-Ga. The assay is performed as follows. First, a mixture is prepared of 20 mM $MgCl_2$, 0.2 mM ATP, 2 mM $NaVO_4$, and 100 µM fluo-Kemptide in a total of 50 µL 40 mM Tris-HCl (pH 7.4). Second, the reaction is initiated by adding 1.0 µL of the enzyme PKA to the mixture; for a control reaction, no PKA is added. Third, the reaction is run overnight at room temperature. Fourth, the reaction and control are diluted 1:1000, and 1 µL of the diluted solution is added to a volume of 49 µL of MM-Ga solution (approximately 30 nM MM-Ga) in a MES buffer (pH 5.5) in a 384-well plate. Fifth, the plate is incubated at room temperature for 60 min. Finally, the luminescence polarization is measured using an ANALYST™ light-detection platform (Molecular Devices Corporation, Sunnyvale, Calif.). These experiments show that the phosphorylated peptide and the MM-Ga bind to one another specifically, i.e., that the phosphorylated Kemptide and the MM-Ga bind together strongly and that the non-phosphorylated Kemptide and the MM-Ga do not bind together appreciably.

Figure 11:
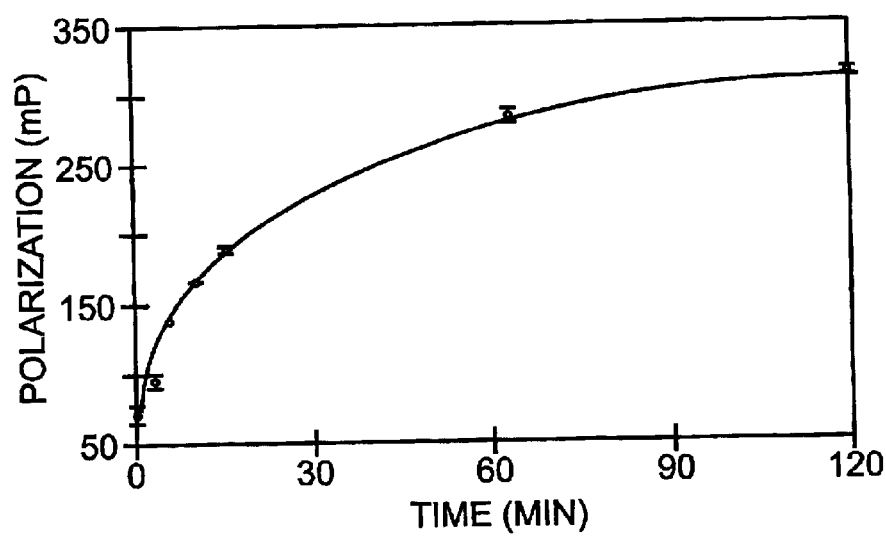
FIG. 11 is a graph showing a time-course assay of PKA activity with MM-Ga performed under the reaction conditions of FIG. 10.

FIG. 11 shows a time-course assay for PKA activity with MM-Ga, performed under the reaction conditions of FIG. 10. At each time point, 1 µL of reaction mixture is taken out from the reaction and immediately diluted into a volume of 1000 µL of MES buffer. Afterwards, 1 µL of each diluted sample is added to a volume of 49 µL of MM-Ga solution, and an assay is conducted as described above.

Example 5

Examples 3 and 4 describe homogeneous assays in which metal ions (e.g., $Ga^{3+}$) immobilized on macromolecules system bind selectively to phosphorylated peptides generated in a kinase reaction. These assays may be used to monitor the time course and/or end point of a kinase (and/or phosphatase) reaction using various luminescence methods, including luminescence polarization.

This example describes a heterogeneous kinase assay in accordance with aspects of the invention. Here, the feasibility of using metal-coated plates in the development of generic kinase assays is demonstrated with a commercial $Ni^{2+}$-coated plate (Pierce, Rockford, Ill.), in which the $Ni^{2+}$ is replaced with $Ga^{3+}$. Specifically, 200 µL of a 0.5 M EDTA-containing solution is added to each well of a 96-well $Ni^{2+}$-coated plate, and the plate is incubated at room temperature for 1 hour. The process is repeated two more times to remove at least substantially all of the $Ni^{2+}$ from the plate. The plate then is washed 3 times with 10 mM Tris buffer (pH 7.4). Next, 200 µL of a 0.1 M $GaCl_3$ solution is added to each well of the plate, and the plate is incubated overnight at room temperature. The plate is washed three times before being used in a kinase assay. This procedure effectively converts the walls of the plate into assay surfaces capable of binding a phosphorylated substrate but not a nonphosphorylated substrate.

Figure 12:
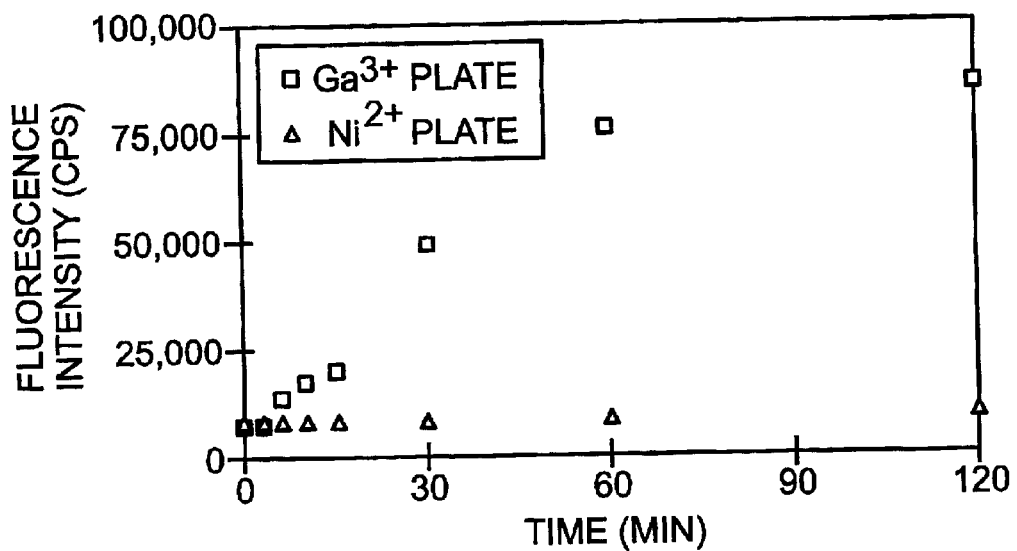
FIG. 12 is a graph showing a time-course assay of PKA activity with a $Ga^{3+}$-coated plate.

FIG. 12 shows results from a kinase assay and an associated control assay. The kinase reaction is set up as described previously, using PKA as the enzyme and fluorescein-Kemptide as the substrate. At each time point, 1 µL is taken from the reaction and diluted into 1000 µL of MES buffer. Later, a volume of 100 µL of each diluted solution is added to the $Ga^{3+}$-coated plate or (as a control) an unmodified $Ni^{2+}$-coated plate and incubated for 1 hour at room temperature. Then, the plate is washed three times, and 100 µL of a 1 M $KH_2PO_4$ solution is added to elute the bound phosphorylated Kemptide from the plate. The luminescence intensity is measured using an ANALYST™ light-detection platform (Molecular Devices Corporation, Sunnyvale, Calif.), which is set in fluorescence intensity mode and fitted with a medium attenuator. The luminescence may be measured from above and/or below the sample, for example, from below the sample by detecting through a lower surface of the sample well that transmits light. In some embodiments, a blocking reagent such as a quencher may be added to the sample to reduce luminescence (and hence background) from unbound components of the sample.

These experiments show the viability of a heterogeneous assay format and the specificity of binding to the tricationic versus dicationic metal ion. The heterogeneous assay format offers many of the advantages of the homogenous assays, including its applicability in principle to any kinase regardless of its substrate specificity. This may save assay developers 3 to 6 months of time and effort in making antibodies that recognize specifically a phosphorylated version of an amino acid sequence. The lack of availability of such special antibodies often is the major obstacle in the development of nonradioactive kinase assays. The heterogeneous assay format also allows for simple detection using luminescence intensity, without requiring polarizers or selection of complementary energy transfer pairs.

Example 6

This example describes assays for the presence, activity, substrates, and/or products of phosphodiesterases in accordance with aspects of the invention. Similar assays may be used to analyze cyclases in which the substrate of the phosphodiesterase reaction becomes the product of the cyclase reaction.

Phosphodiesterases (PDEs) catalyze the decyclization of cyclic nucleotides to the corresponding noncyclized nucleotide monophosphate, as shown below:

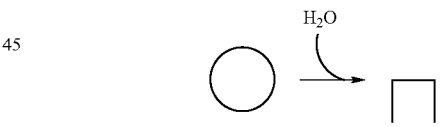

Thus, the presence and/or activity of a PDE may be detected by a decrease in the concentration of a cyclic nucleotide (cNMP) substrate and/or by an increase in the concentration of a corresponding uncyclized nucleotide monophosphate (NMP) product. (The presence and/or activity of a cyclase may be detected similarly by a decrease in the concentration of a nucleotide triphosphate substrate and/or by an increase in the concentration of a corresponding cyclic nucleotide.) The invention provides among others PDE assays that involve contacting a sample containing a candidate PDE (and optionally a modulator thereof) with a luminescently labeled cyclic nucleotide and a binding partner that binds specifically to the corresponding uncyclized nucleotide monophosphate but not to the cyclic nucleotide. The binding partner may include one or more of the attributes described above, such as a tricationic metal $M^{3+}$ (e.g., $Al^{3+}$, $Ga^{3+}$, and/or $Fe^{3+}$) capable of binding an uncyclized phosphate group but not a cyclized phosphate group, and optionally an energy transfer partner and/or quencher. PDE activity may be detected by an increase in NMP binding using any technique capable of measuring such an increase, including luminescence polarization, luminescence resonance energy transfer, luminescence intensity, and/or nonluminescence and/or heterogeneous techniques, among others. For example, PDE activity may be detected following NMP binding by (1) an increase in luminescence polarization (assuming that the lifetime and rotational correlation time of the binding partner are selected so that binding of the NMP to the binding partner measurably decreases the rotational correlation time of the NMP), (2) an increase in luminescence resonance energy transfer (assuming that the binding partner is associated with a suitable energy transfer partner), and/or (3) a decrease in luminescence intensity (assuming that the binding partner is associated with a suitable luminescence quencher).

The assays may include (1) contacting a sample containing a candidate PDE (and/or other cell-signaling component) with a luminescently labeled cyclic nucleotide and a binding partner capable of distinguishing between the cyclic nucleotide and the corresponding nucleotide monophosphate, (2) illuminating the sample with light capable of inducing luminescence in the sample, (3) measuring a property of the luminescence transmitted from the sample, and (4) correlating the property with the presence and/or activity of the cyclic nucleotide and/or the corresponding nucleotide monophosphate and hence the presence and/or activity of an associated enzyme.

The invention also provides methods for identifying modulators such as agonists and inhibitors of receptors and/or enzymes involved in the production and/or regulation of cell-signaling molecules, such as the hydrolysis of cyclic nucleotides. The methods may include looking for the effects of a modulator by conducting a method for determining the concentration of a cyclic nucleotide and/or the corresponding nucleotide monophosphate in both the presence and absence of the putative modulator. For example, in a polarization assay in which PDE activity leads to an increase in polarization, a decrease in the measured extent of polarization of the emitted light in the presence of the putative modulator identifies the putative modulator as an inhibitor of the receptor or enzyme, and an increase in the measured extent of polarization in the presence of the putative modulator identifies the putative modulator as an agonist of the receptor or enzyme.

Example 7

This example describes end-point and time-course assays for PDE 5 in accordance with aspects of the invention, showing in part the utility of the MM-Ga system in PDE assays. These assays use the following components, among others: (1) cGMP-specific PDE (type V, Calbiochem, La Jolla, Calif.), (2) N-methylanthraniloyl (MANT) cGMP substrate (Molecular Probes, Eugene, Oreg.), and (3) MM-Ga, as described in Example 1. MANT is a compact blue-fluorescing luminophore that attaches to the cGMP via the ribose ring of the cGMP. These assays show the utility of the MM-Ga system for detection of noncyclized GMP and the presence and/or activity of cGMP-specific PDEs.

Figure 13:
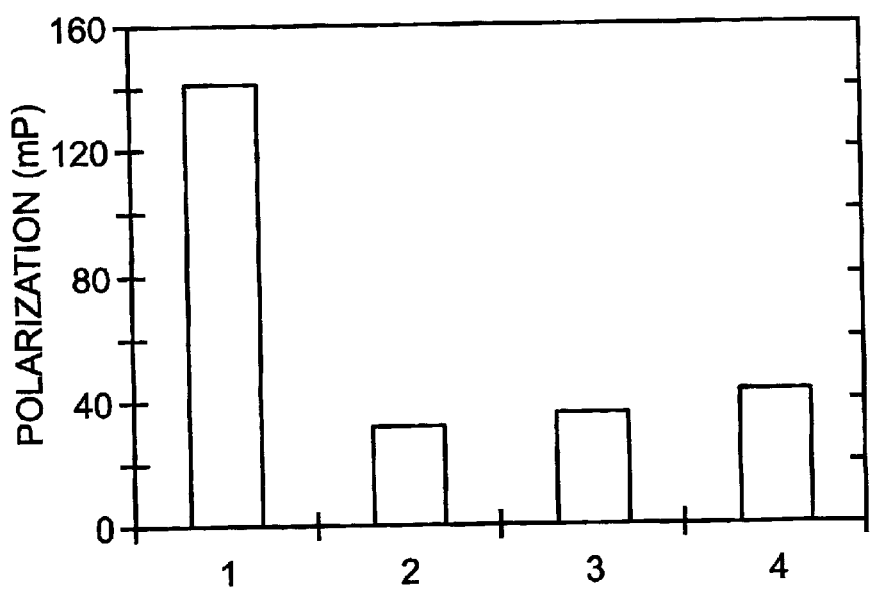
FIG. 13 is a bar graph showing results from an end-point study for cGMP PDE activity using MANT-cGMP and MM-Ga under the following conditions: (1) reaction with enzyme, with MM-Ga, (2) reaction with enzyme, without MM-Ga (3) reaction without enzyme, with MM-Ga (4) reaction without enzyme, without MM-Ga.

FIG. 13 shows results of an end-point assay. Here, 1 µL (50 units) of cGMP specific PDE is added to 50 µL of 5 µM MANT-cGMP in a HEPES buffer (pH 7.5). The tube is incubated at room temperature for 60 minutes. Then, 10 µL of the reaction mixture is added to 40 µL of MES/BSA buffer (pH 5.5) containing approximately 0.8 µM MM-Ga. The resulting mixture is incubated at room temperature for 30 minutes. Then, the luminescence polarization is measured (for MANT, excitation 360 nm, emission 480 nm) using an ANALYST™ light-detection platform (Molecular Devices Corporation, Sunnyvale, Calif.). Results correspond to the following conditions: (1) reaction with enzyme, with MM-Ga, (2) reaction with enzyme, without MM-Ga (3) reaction without enzyme, with MM-Ga, and (4) reaction without enzyme, without MM-Ga. These experiments show that the cyclic GMP and the MM-Ga bind to one another specifically.

Figure 14:
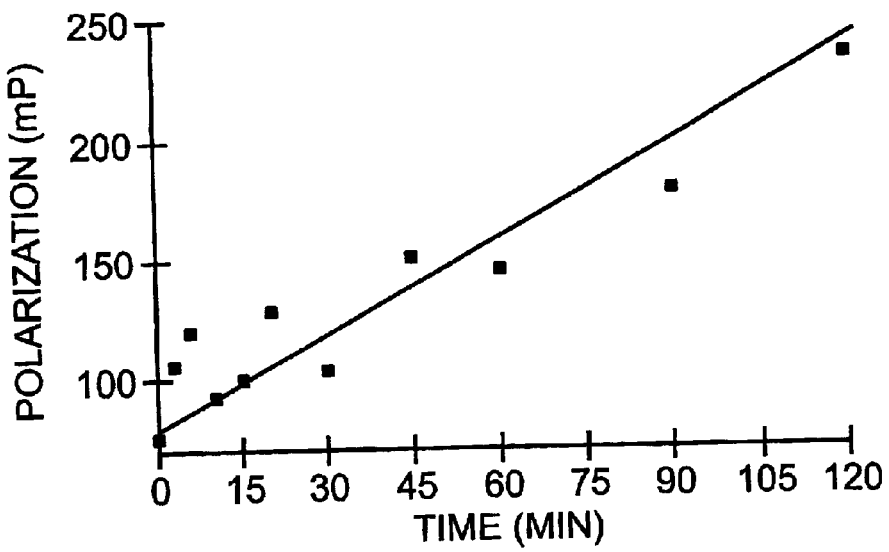
FIG. 14 is a graph showing results from a time-course study conducted using the system of FIG. 13.

FIG. 14 shows results of a time-course assay. Here, a 50-µL solution containing 100 µM MANT-cGMP and 100 units of PDE in HEPES buffer (pH 7.5) is incubated at room temperature. At each time point, 2 µL of reaction mixture is removed from the tube and diluted into 200 µL of MES/BSA buffer (pH 5.5). After 2 hours, 45 µL of each it diluted reaction solution is mixed with 5 µL of MM-Ga (approx. 6.4 µM) and incubated at room temperature for 30 minutes before the fluorescence polarization is measured.

Example 8

This example describes alternative PDE assays in accordance with aspects of the invention. These assays are presented in a homogenous, nonradioactive format using a carboxyfluorescein labeled cGMP substrate. The assay also may be used in a heterogeneous format and/or with an alternative luminescent cGMP and/or cAMP. These assays further show the utility of the MM-Ga system for detection of noncyclized GMP and the presence and/or activity of cGMP-specific PDEs, including the use of a different luminophore than the MANT of Example 7.

Figure 15:
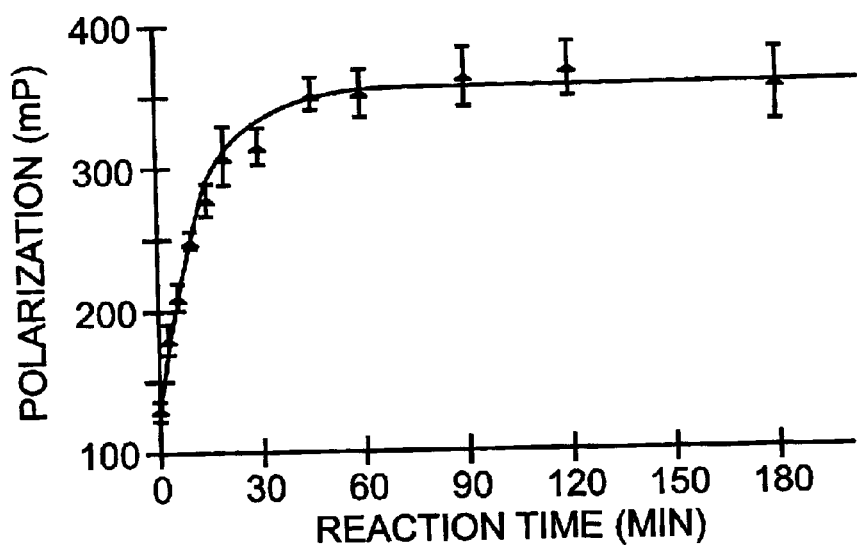
FIG. 15 is a graph showing results from a time-course study for cGMP PDE activity using fluorescein-cGMP and MM-GA.

FIG. 15 shows results of a time-course assay conducted using fluorescein-cGMP and the PDE and binding partner of Example 7. Here, 2.0 µM fluorescein-cGMP is incubated with 0.5 unit of PDE (V) in a buffer containing 40 mM MOPS (pH 7.5), 0.5 mM EDTA, 15 mM $MgCl_2$, and 0.15 mg/mL BSA in a total volume of 50 µL. At each time point, 1 µL of the reaction mixture is removed and diluted into 200 µL of MES buffer (pH 5.5), and the diluted solution is placed on ice. After the reaction, 25 µL of the diluted solution is mixed with an equal volume of a MM-Ga solution, and incubated at room temperature for 30 minutes before the luminescence polarization value is measured.

Figure 16:
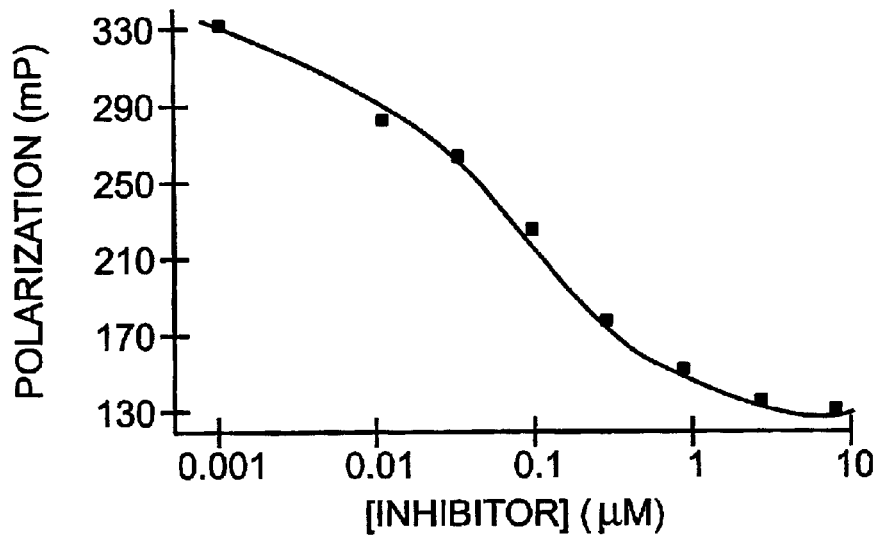
FIG. 16 is a graph showing an IC50 measurement of Zaprinast using the system of FIG. 15.

FIG. 16 shows results of an inhibition assay using the components of FIG. 15. Here, the assay was used to measure the IC50 of the known PDE (V) inhibitor, Zaprinast, using 0.5 µM fluorescein-cGMP and a reaction time of 30 min. These experiments show that the IC50 is about 0.1 µM, in reasonable agreement with the literature value of about 0.3 µM determined using a radioactive assay with $^3H$-cGMP as the substrate.

Example 9

This example describes several aspects of the invention, including (1) use of $Ga^{3+}$-coated nanoparticles as the binding component in the assay, (2) applications to the detection of PDE 4 enzyme, with fluorescein-labeled cAMP as substrate, and (3) applications to the detection of PDE 1 enzyme, with both fluorescein-labeled cAMP and fluorescein-labeled cGMP as substrates.

As discussed in Example 1, synthetic polymer macromolecules (MM) can be substituted with other materials that have a high molecular weight and that tricationic cations (i.e., $Fe^{3+}$, $Ga^{3+}$) can be immobilized on. Here, we use selected nanoparticles, including polystyrene nanoparticles having an average diameter of about 40 nm. The nanoparticles are from Bangs Laboratory (Fisher, Ind.), and are modified after acquisition from the vendor to attach $Ga^{3+}$ on the surfaces of the particles.

Figure 17:
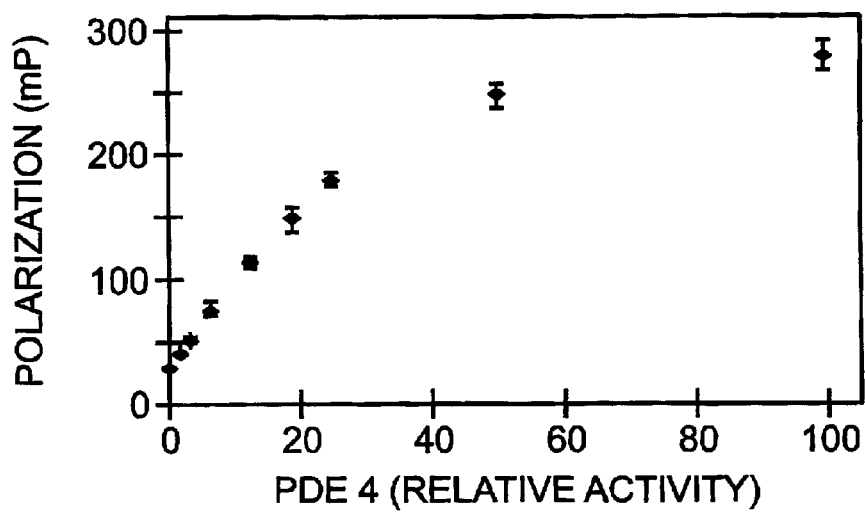
FIG. 17 is a graph showing the detection of PDE 4 activity using a fluorescein-labeled cAMP substrate.

FIG. 17 shows the detection of PDE 4 activity using a fluorescein-labeled cAMP (FL-cAMP) substrate. PDE 4 was obtained from Dr. Macro Conti at Stanford University. In this assay, 10 μL of a solution containing 40 nM of FL-cAMP is mixed with 10 μL of a series of solutions containing various concentrations of PDE 4 in a black 384-well plate. The mixture is incubated at room temperature for 45 min, and then 60 μL of a solution containing 0.16 mg/mL of the modified nanoparticles is added. The new mixture is incubated for 30 min, and then the luminescence polarization is measured.

Figure 18:
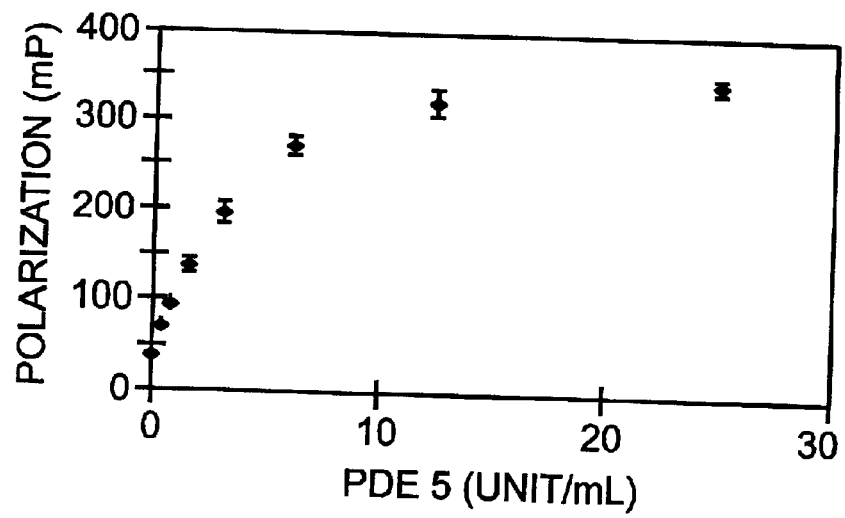
FIG. 18 is a graph showing the detection of PDE 5 activity using a fluorescein-labeled cGMP substrate using the conditions of FIG. 17.

FIG. 18 shows similar results using PDE 5 (Calbiochem, La Jolla, Calif.) as the enzyme and a fluorescein-labeled cGMP (FL-cGMP) as the substrate under the conditions of FIG. 17.

Figure 19:
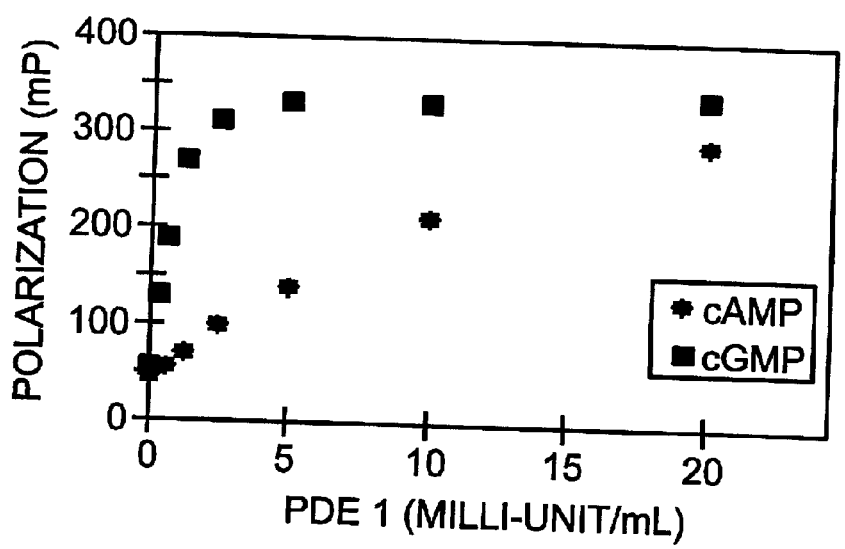
FIG. 19 is a graph showing the detection of PDE 1 activity using fluorescein-labeled cAMP and fluorescein-labeled cGMP substrates under the conditions of FIG. 17.

FIG. 19 shows similar results using PDE 1 (Sigma, St. Louis, Mo.) as the enzyme and both FL-cAMP and FL-cGMP as substrates under the conditions of FIG. 17. PDE 1 is another isozyme in the PDE family of enzymes, which acts on both FL-cAMP and FL-cGMP. The PDE 1 used here is activated according to the vendor's instructions.

Example 10

This example shows representative tracers for use in cyclic nucleotide assays, particularly luminescence-polarization-based cyclic nucleotide assays. General structures for such tracers are shown below for (A) cAMP and (B) cGMP:

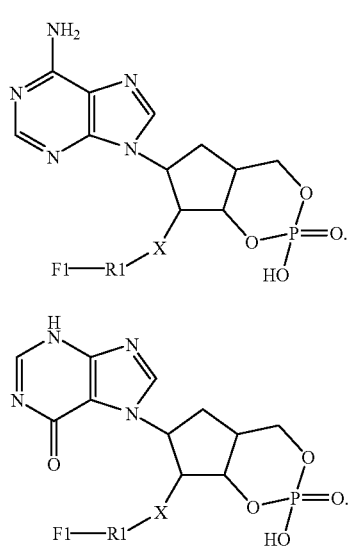

Here, X and R1 represent linkers, which optionally and independently may be present or absent, and F1 represents a reporter species. X may include among others any alkyl, allyl, or aryl linker with ester or ether bonds to the cyclic nucleotide, including —OC(=O)—CH$_2$CH$_2$C(=O)—. R1 may be any linker joining FL to the nucleotide, directly, or indirectly through X, including a rigid linker having (two) reactive groups for coupling, one to FL and one to the nucleotide. For example, R1 may be a diamino-alkyl, -cycloalkyl, -aryl, or -allyl group, or a dihydroxy group that forms an amide or ester, respectively, with the groups X and F1. F1 may include any suitable reporter species, such as a luminophore for luminescence assays or an isotope for radioassays. For example, F1 may include a fluorescein or rhodamine that forms a thiourea, ester, or amide bond with the group X. Preferred structures include 1,2 and 1,4-diaminocyclohexyl-linked tracers, as described in U.S. patent application Ser. No. 09/768,661, filed Jan. 23, 2001, which is incorporated herein by reference.

Example 11

This example describes methods and kits for detecting phosphate modifications and/or associated enzymes and modulators in whole cells. The methods generally comprise growing cells under desired conditions, lysing the cells, incubating the cells before and/or after lysis with one or more reagents, and detecting the presence, quantity, and/or activity of species and/or reactions of interest. The kits generally comprise collections of reagents and/or other materials of interest, including substrates, binding partners, and/or lysis buffers, among others. The methods and kits are described greater detail in the context of cyclic nucleotide assays for adherent and suspended cells in Examples 8 and 9 of U.S. patent application Ser. No. 09/768,661, filed Jan. 23, 2001, which is incorporated herein by reference.

Example 12

This example describes miscellaneous applications and other uses for the various assays described herein.

The applications include detecting any of the modifications, enzymes, and/or modulators identified herein and/or in the following U.S. patent applications, which are incorporated herein by reference: Ser. No. 09/768,661, filed Jan. 23, 2001; and Ser. No. 09/596,444, filed Jun. 19, 2000. The modifications include phosphorylation, dephosphorylation, cyclization, and/or decyclization, among others, as described above. The enzymes include kinases, phosphatases, cyclases, and/or phosphodiesterases, among others, including variants such as isoenzymes thereof. For example, the cyclases include adenylyl cyclase and guanylyl cyclase, among others, and the phosphodiesterases include PDE 1 through PDE 10, among others. The modulators include modulators of these enzymes, among others. For example, the cyclase modulators include forskolin and ODQ, among others, and the phosphodiesterase modulators include cilostamide, dipyridamole, EHNA hydrochloride, etazolate hydrochloride, MBCQ, MMPX, MY-5445, Ro 20-1724, rolipram, siguazodan, vinpocetine, and Zaprinast, among others.

The applications also include combining assays for different modifications, enzymes, and/or modulators to form integrated assays, for example, by combining a phosphorylation assay and a cyclization assay to study signaling mechanisms involving multiple cell-signaling pathways.

Example 13

This example describes kits for use in performing assays in accordance with aspects of the invention. The kits may include substrates and/or binding partners for performing the assays described herein. These substrates and/or binding partners may include luminophores, quenchers, and/or energy transfer partners, among others. The kits also may include sample holders such as microplates or biochips that have been treated to act as binding partners. The kits optionally may include additional reagents, including but not limited to buffering agents, luminescence calibration standards, enzymes, enzyme substrates, nucleic acid stains, labeled antibodies, or other additional luminescence detection reagents. The substrates, binding partners, and/or additional reagents optionally are present in pure form, as concentrated stock solutions, or in prediluted solutions ready for use in the appropriate energy transfer assay. Typically, the kit is designed for use in an automated and/or high-throughput assay, and so is designed to be fully compatible with microplate readers, microfluidic methods, and/or other automated high-throughput methods.

Example 14

This example describes exemplary luminescence assays. Further aspects of these assays as well as additional luminescence assays and apparatus for performing luminescence assays are described in the following materials, which are incorporated herein by reference: U.S. Pat. No. 6,097,025, issued Sep. 24, 1998; U.S. patent application Ser. No. 09/349,733, filed Jul. 8, 1999; U.S. Provisional Patent Application Ser. No. 60/267,639, filed Feb. 10, 2001; and Joseph R. Lakowicz, *Principles of Fluorescence Spectroscopy* ($2^{nd}$ ed. 1999).

Luminescence, as defined above, is the emission of light from excited electronic states of atoms or molecules, including photoluminescence, chemiluminescence, and electrochemiluminescence, among others. Luminescence may be used in a variety of assays, including (A) intensity assays, (B) polarization assays, and (C) energy transfer assays, among others.

A. Intensity Assays

Luminescence intensity assays involve monitoring the intensity (or amount) of light emitted from a composition. The intensity of emitted light will depend on the extinction coefficient, quantum yield, and number of luminescent analytes in the composition, among others. These quantities, in turn, will depend on the environment of the analyte, among others, including the proximity and efficacy of quenchers and energy transfer partners. Thus, luminescence intensity assays may be used to study binding reactions, among other applications.

B. Polarization Assays

Luminescence polarization assays involve the absorption and emission of polarized light. Here, polarization refers to the direction of the light's electric field, which generally is perpendicular to the direction of the light's propagation. In a luminescence polarization assay, specific molecules within a composition are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size, shape, and environment of the reorienting molecule. Thus, luminescence polarization assays may be used to quantify binding reactions and enzymatic activity, among other applications. In particular, molecules commonly rotate (or "tumble") via diffusion, with a rotational correlation time $\tau_{rot}$ that is proportional to their volume, or the cube of their radius of gyration. (This cubic dependence on radius makes polarization assays very sensitive to binding.) Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \quad (1)$$

Here, P is the polarization, $I_\|$ is the intensity of luminescence polarized parallel to the polarization of the excitation light, and $I_{195}$ is the intensity of luminescence polarized perpendicular to the polarization of the excitation light. P generally varies from zero to one-half for randomly oriented molecules (and zero and one for aligned molecules). If there is little rotation between excitation and emission, $I_{81}$ will be relatively large, $I_\perp$ will be relatively small, and P will be close to one-half. (P may be less than one-half even if there is no rotation; for example, P will be less than one-half if the absorption and emission dipoles are not parallel.) In contrast, if there is significant rotation between absorption and emission, $I_\|$ will be comparable to $I_{195}$, and P will be close to zero. Polarization often is reported in milli-P units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\| - I_\perp}{I_\| + 2I_\perp} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 daltons and 4,000,000 daltons.

Luminescence polarization assays may be used in a variety of formats. In one format, the concentration of an analyte in solution can be measured by supplying a labeled tracer that competes with the analyte for a binding moiety, particularly a binding moiety larger than the labeled tracer. In this "competitive" format, the concentration of the analyte is inversely correlated with the enhancement of luminescence polarization in the light emitted by the tracer when it competitively binds the common moiety. In another format, the concentration of a target can be measured by supplying a labeled tracer that is capable of binding the target. In this case, the enhancement of polarization is a direct measure of the concentration of target. The target further may be, for example, an activated receptor, where activation can be indirectly measured by the directly measured concentration of a generated molecule or by its binding to labeled tracer per se.

C. Energy Transfer Assays

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The efficiency of this transfer is very sensitive to the separation R between donor and acceptor, decaying as $1/R^{-6}$. Energy transfer assays use energy transfer to monitor the proximity of donor and acceptor, which in turn may be used to monitor the presence or activity of an analyte, among others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction. In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleave by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

Example 15

This example shows assays with improved signals, signal-to-noise ratios, and/or signal-to-background ratios.

Signal may be enhanced in several ways, including (1) using a high color temperature light source, such as a xenon arc lamp, in a continuous illumination mode, (2) using a dichroic or multi-dichroic beamsplitter, and/or (3) using a sample holder whose shape is "matched" to the shape of the optical beam of the instrument, especially if the sample holder is elevated to bring the sample closer to a detector. The high color temperature light source increases the number of usable photons, which is important because the lower limit of the signal-to-noise ratio is set by the square root of the total number of photons collected in the measurement. These enhancements are described in more detail in the following U.S. patent applications, which are incorporated herein by reference: Ser. Nos. 09/349,733, filed Jul. 8, 1999; 09/478,819, filed Jan. 5, 2000; and Ser. No. 09/494,407, filed Jan. 28, 2000.

Signal-to-noise ratios can be enhanced at least in part by increasing signals, for example, by using the techniques described in the previous paragraph.

Signal-to-background ratios can be enhanced in several ways, including (1) using confocal optical systems having a sensed volume to avoid luminescence from the microplate walls, (2) selecting a microplate or other substrate that increases the signal and reduces the luminescent background from materials in the microplate, (3) selecting the light sources, luminescence filters, optics, signal collection electronics, and mechanical system used in the luminescence detection optical system for maximum signal-to-background ratio, and (4) utilizing signal processing, background subtraction, and luminescence lifetime techniques, particularly FLAMe™ methodology for background reduction, as described below. These enhancements are described in more detail in the following U.S. patent and U.S. patent applications, which are incorporated herein by reference: U.S. Pat. No. 6,071,748, issued Apr. 17, 1998; Ser. Nos. 09/349,733, filed Jul. 8, 1999; Ser. No. 09/478,819, filed Jan. 5, 2000; and Ser. No. 09/494,407, filed Jan. 28, 2000.

Example 16

This example shows mechanisms for increasing the change in polarization that accompanies a change in binding, so that the change in binding can be measured more easily. These mechanisms may be used in any of the assays described here involving luminescently labeled species, such as labeled cyclic nucleotides and labeled nonhydrolyzable GTP analogs, among others.

The change in polarization upon binding can be increased by making any linker between the luminophore and the labeled species (e.g., the cyclic nucleotide or GTP analog) as short and/or rigid as possible, while maintaining relevant substrate properties for the enzymes involved in the assay. Short and/or rigid linkers will restrict luminophore motion relative to the labeled species, reducing the "propeller effect" so that the luminophore more accurately reports the motion of both the free and bound labeled species. The rigidity of the linker may be increased by avoiding using hexanoic acid linkers, which typically are long and flexible, and by using cyclic linkers and amide groups in place of methylene groups, among other mechanisms.

The change in polarization upon binding also can be increased by including an appropriately positioned energy transfer acceptor on the binding partner, so that energy transfer will occur from the luminophore to the acceptor upon incorporation. Such energy transfer will shorten the lifetime of the luminophore, thereby increasing its polarization (because polarization varies inversely with lifetime, all else being equal).

The change in polarization upon binding also can be increased by decreasing the mobility of the binding partner for the labeled species. Mobility can be decreased by increasing the size of the binding partner, either directly or by forming a complex with a mass label. Suitable mass labels include other molecules and beads, among others. The use of mass labels is described in detail in U.S. patent application Ser. No. 09/768,742, filed Jan. 23, 2001, which is incorporated herein by reference. Mobility also can be decreased by attaching the binding partner to a surface, such as the surface of a sample holder. Attachment to other molecules, beads, and/or surfaces may be accomplished using any of a number of well-known reactive groups.

The assays provided by the invention may have advantages over prior assays for detecting molecular modifications. The existence and/or identity of these advantages will depend on such as (but not always requiring) one or more of the following. First, they may be used without radioactivity. Second, they may be homogenous, so that they do not require physical separation steps or wash steps. Third, they may have stable endpoints, so that results are relatively insensitive to the timing of any measurement or detection steps. Fourth, they may be sensitive, so that picomolar amounts of cyclic nucleotides may be detected. Fifth, they may be used with solution and cell-based samples.

The disclosure set forth above encompasses multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious and directed to one of the inventions. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed through amendment of the present claims or through presentation of new claims in this or a related application. Such claims, whether directed to a different invention or to the same invention, and whether broader, narrower, equal, or different in scope to the original claims, also are regarded as included within the subject matter of the inventions of the present disclosure.

---

---

We claim:

1. A method of detecting the activity of an enzyme that performs a phosphate modification on a substrate to form a product in a sample, comprising:
   contacting the substrate with the enzyme in the sample;
   contacting the sample with a binding partner that specifically binds to the substrate or to the product, but not to both, wherein the binding partner includes Ga(III) ion that is required for binding between the binding partner and the substrate or the product;
   detecting a response, based on luminescence polarization, indicative of the extent of binding between the substrate or the product and the binding partner without separating the bound substrate or product from the unbound substrate or product; and correlating the response with the activity of the enzyme.

2. The method of claim 1, wherein the step of detecting a response comprises:
   exposing the sample to polarized light; and
   measuring the degree of polarization of light emitted from the sample, in response to the step of exposing, wherein the degree of polarization is indicative of the extent of binding between the substrate or product and the binding partner.

3. The method of claim 2, further comprising determining the degree of polarization of the emitted light using a function selected from the group consisting of polarization and anisotropy.

4. The method of claim 1, wherein the substrate is a polypeptide, and wherein the substrate and product are related by phosphorylation or dephosphorylation of the polypeptide.

5. The method of claim 4, wherein the substrate and product are luminescent.

6. The method of claim 5, wherein the enzyme is a kinase, wherein the product is related to the substrate by phosphorylation of the substrate, wherein the binding partner specifically binds to the product but not to the substrate, and wherein the degree of polarization of light emitted from the sample is higher when the enzyme is operative to form the product from the substrate than when the enzyme is inoperative or absent.

7. The method of claim 5, wherein the enzyme is a phosphatase, wherein the product is related to the substrate by dephosphorylation of the substrate, wherein the binding partner specifically binds to the substrate but not to the product, and wherein the degree of polarization of light emitted from the sample is lower when the enzyme is operative to form the product from the substrate than when the enzyme is inoperative or absent.

8. The method of claim 1, wherein the substrate is a nucleotide, and wherein the substrate and product are related by a cyclization or decyclization of the nucleotide.

9. The method of claim 8, wherein the substrate and product are luminescent.

10. The method of claim 9, wherein the enzyme is a phosphodiesterase, wherein the substrate is a cyclic nucleotide, wherein the product is a nucleotide monophosphate formed by decyclization of the substrate, wherein the binding partner specifically binds to the product but not to the substrate, and wherein the degree of polarization of light emitted from the sample is higher when the enzyme is operative to form the product from the substrate than when the enzyme is inoperative to absent.

11. The method of claim 9, wherein the enzyme is a cyclase, wherein the substrate is a nucleotide monophosphate, wherein the product is a cyclic nucleotide formed by cyclization of the substrate, wherein the binding partner specifically binds to the substrate but not to the product, and wherein the degree of polarization of light emitted from the sample is lower when the enzyme is operative to form the product from the substrate than when the enzyme is inoperative or absent.

12. The method of claim 1, wherein the enzyme is selected from the group consisting of kinases and phosphatases.

13. The method of claim 1, wherein the enzyme is selected from the group consisting of cyclases and phosphodiesterases.

14. The method of claim 1, wherein the substrate includes a phosphorylated polypeptide or a nonphosphorylated polypeptide.

15. The method of claim 1, wherein the substrate includes a cyclized nucleotide or a noncyclized nucleotide.

16. The method of claim 1, further comprising:

contacting the substrate and enzyme with a candidate compound; and determining the ability of the candidate compound to enhance or inhibit enzyme activity by its effects on the response.

17. The method of claim 1, the binding between the binding partner and the substrate or product being characterized by a binding coefficient, wherein the binding coefficient is no larger than about $10^{-8}$ M.

18. The method of claim 1, further comprising:

providing a sample holder having a plurality of sample sites supporting a corresponding plurality of samples; and repeating the steps of contacting, detecting, and correlating for each of the plurality of samples.

19. The method of claim 1, wherein the step of contacting the substrate with the enzyme precedes the step of contacting the sample with a binding partner.

20. The method of claim 1, the step of contacting the substrate with the enzyme catalyzing a reaction that forms the product, wherein the response is determined at least substantially at an end point of the reaction.

21. The method of claim 1, the step of contacting the substrate with the enzyme catalyzing a reaction that forms the product, wherein the response is determined at different times along the time course of the reaction.

* * * * *